United States Patent
Moussy et al.

(10) Patent No.: US 7,718,676 B2
(45) Date of Patent: May 18, 2010

(54) 2-AMINOARYLOXAZOLE COMPOUNDS AS TYROSINE KINASE INHIBITORS

(75) Inventors: Alain Moussy, Paris (FR); Camille Wermuth, Strasbourg (FR); David Grierson, Versailles (FR); Abdellah Benjahad, Champigny sur Marne (FR); Martine Croisy, Cernay la Ville (FR); Marco Ciufolini, Lyons (FR); Bruno Giethlen, Illkirch (FR)

(73) Assignees: AB Science, Paris (FR); Centre National de la Recherche Scientifique (CNRS), Paris (FR); Institut Curie, Paris (FR)

( * ) Notice: Subject to any disclaimer, the term of this patent is extended or adjusted under 35 U.S.C. 154(b) by 764 days.

(21) Appl. No.: 10/576,267

(22) PCT Filed: Oct. 22, 2004

(86) PCT No.: PCT/IB2004/003698

§ 371 (c)(1),
(2), (4) Date: Apr. 18, 2006

(87) PCT Pub. No.: WO2005/040139

PCT Pub. Date: May 6, 2005

(65) Prior Publication Data

US 2007/0142390 A1 Jun. 21, 2007

Related U.S. Application Data

(60) Provisional application No. 60/513,214, filed on Oct. 23, 2003.

(51) Int. Cl.
*A61K 31/44* (2006.01)
*A61K 31/422* (2006.01)
*C07D 263/30* (2006.01)
*C07D 413/04* (2006.01)

(52) U.S. Cl. ............... 514/340; 544/358; 544/360; 544/364; 546/268.1; 546/271.4; 548/215; 548/234; 514/253.01; 514/336; 514/377

(58) Field of Classification Search ............... 544/358, 544/359, 360, 364; 548/215, 233, 234; 514/252.12, 514/252.13, 253.01, 374, 377, 336, 340; 546/268.1, 271.4
See application file for complete search history.

(56) References Cited

U.S. PATENT DOCUMENTS

| 5,000,775 | A | 3/1991 | Grabiak et al. | |
|---|---|---|---|---|
| 6,331,553 | B1 * | 12/2001 | Esaki et al. | 514/352 |
| 6,399,773 | B1 * | 6/2002 | Liu et al. | 544/106 |
| 6,596,747 | B2 * | 7/2003 | Liu et al. | 514/374 |

FOREIGN PATENT DOCUMENTS

| EP | 0 254 259 A2 | 1/1988 |
|---|---|---|
| EP | 0 949 242 A1 | 10/1999 |
| WO | WO 02/45652 A2 | 6/2002 |
| WO | WO 04/001059 A2 | 12/2003 |
| WO | WO 2004/032882 A2 | 4/2004 |
| WO | WO 2005/000298 A2 | 1/2005 |

OTHER PUBLICATIONS

Murali et al., "A Modified Approach to 2-(N-Aryl)-1,3-oxazoles", *Organic Letters*, vol. 4, No. 12, 2002, pp. 2091-2093.
Nath et al., "Synthesis and Mercuration of Some New 2-arylamino-4,5-disubstituted Oxazoles as Pesticides", *Indian Journal of Chemistry, Section B: Organic Chemistry Including Medicinal Chemistry*, vol. 20(B), No. 9, 1981, pp. 827-829.
Rao et al., "Synthesis and fungitoxicity of substituted pyrazolyloxazole", *Journal of the Indian Chemical Society*, vol. 58, No. 9, 1981, pp. 925-926.

* cited by examiner

*Primary Examiner*—Golam M Shameem
(74) *Attorney, Agent, or Firm*—Foley & Lardner LLP

(57) ABSTRACT

The present invention relates to novel compounds selected from 2-aminoaryloxazoles of formula I that selectively modulate, regulate, and/or inhibit signal transduction mediated by certain native and/or mutant tyrosine kinases implicated in a variety of human and animal diseases such as cell proliferative, metabolic, allergic, and degenerative disorders. More particularly, these compounds are potent and selective c-kit, bcr-abl, FGFR3 and/or Flt-3 inhibitors.

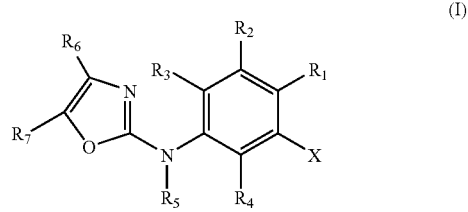

(I)

17 Claims, No Drawings

2-AMINOARYLOXAZOLE COMPOUNDS AS TYROSINE KINASE INHIBITORS

The present invention relates to novel compounds selected from 2-aminoaryloxazoles that selectively modulate, regulate, and/or inhibit signal transduction mediated by certain native and/or mutant tyrosine kinases implicated in a variety of human and animal diseases such as cell proliferative, metabolic, allergic, and degenerative disorders. More particularly, these compounds are potent and selective c-kit, bcr-abl, FGFR3 and/or Flt-3 inhibitors.

Tyrosine kinases are receptor type or non-receptor type proteins, which transfer the terminal phosphate of ATP to tyrosine residues of proteins thereby activating or inactivating signal transduction pathways. These proteins are known to be involved in many cellular mechanisms, which in case of disruption, lead to disorders such as abnormal cell proliferation and migration as well as inflammation.

As of today, there are about 58 known receptor tyrosine kinases. Included are the well-known VEGF receptors (Kim et al., Nature 362, pp. 841-844, 1993), PDGF receptors, c-kit, Flt-3 and the FLK family. These receptors can transmit signals to other tyrosine kinases including Src, Raf, Frk, Btk, Csk, Abl, Fes/Fps, Fak, Jak, Ack, etc.

Among tyrosine kinase receptors, c-kit is of special interest. Indeed, c-kit is a key receptor activating mast cells, which have proved to be directly or indirectly implicated in numerous pathologies for which the Applicant filed WO 03/004007, WO 03/004006, WO 03/003006, WO 03/003004, WO 03/002114, WO 03/002109, WO 03/002108, WO 03/002107, WO 03/002106, WO 03/002105, WO 03/039550, WO 03/035050, WO 03/035049, WO 03/0720090, WO 03/072106 and IB2004/000907, as well as U.S. 60/495,088.

It was found that mast cells present in tissues of patients are implicated in or contribute to the genesis of diseases such as autoimmune diseases (rheumatoid arthritis, inflammatory bowel diseases (IBD)) allergic diseases, bone loss, cancers such as solid tumors, leukaemia and GIST, tumor angiogenesis, inflammatory diseases, interstitial cystitis, mastocytosis, graft-versus-host diseases, infection diseases, metabolic disorders, fibrosis, diabetes and CNS diseases. In these diseases, it has been shown that mast cells participate in the destruction of tissues by releasing a cocktail of different proteases and mediators such as histamine, neutral proteases, lipid-derived mediators (prostaglandins, thromboxanes and leucotrienes), and various cytokines (IL-1, IL-2, IL-3, IL-4, IL-5, IL-6, IL-8, TNF-α, GM-CSF, MIP-1a, MIP-1b, MIP-2 and IFN-γ).

The c-kit receptor can also be constitutively activated by mutations leading to abnormal cell proliferation and development of diseases such as mastocytosis (D816V mutation) and various cancers such as GIST (c-kitΔ27, a juxtamembrane deletion).

Furthermore, 60% to 70% of patients presenting with AML have blasts which express c-kit, the receptor for stem cell factor (SCF) (Broudy, 1997). SCF promotes growth of hematopoietic progenitors, and act as a survival factor for AML blasts. In some cases (1 to 2%) of AML, a mutation in a conserved residue of the kinase domain (Kit816) resulting in constitutive activation of c-kit has been described (Beghini et al., 2000; Longley et al., 2001). This gain of function mutation (Asp to Val/Tyr substitution) has been identified in mast cell leukemic cell lines and in samples derived from patients with mastocytosis (Longley et al., 1996).

We have studied about 300 patients afflicted with systemic mastocytosis and we have shown that the Kit816 mutation is expressed in about 60% of cases. In this regard, we filed IB 2004/000907 which relates to tailored treatment of the different forms of mastocytosis depending on the presence or absence of the Kit816 mutation.

In view of the above, we have proposed to target c-kit to deplete the mast cells responsible for these disorders.

In addition, 60 to 80% of AML blasts express a similar receptor Flt3, the receptor for Flt3 ligand and in a high percentage of ALL. Both ligand and receptor have been identified by Hannum et al., 1994 and Rosnet et al., 1991. Like the c-Kit, Flt3 mediates differentiation and proliferation of normal hematopoietic stem cells and mediates proliferation and survival signals in AML blasts. Although Flt3 is most commonly expressed in the wild type form, the leukemic clone of 30 to 35% of patients with AML (Nakao et al., 1996), expresses a mutated form of Flt3 that contains an Internal Tandem Duplication (Flt3ITD) of the juxtamembrane domain coding sequence. This mutation leads to constitutive activation of the receptor and autonomous cytokine-independent growth. It has also been reported that a cohort of AML patients (~7%) contains mutations in the activation loop of Flt3 at amino acid position Asp835 (FLT3835) (Yamamoto et al., 2001). This mutation occurs at the corresponding position in c-kit (Kit816) described above, leading kinases to adopt an activated configuration. Flt3 mutations have also been reported at a frequency of 15% in secondary AML and may be associated with disease progression or relapse of AML.

Here, we provide for the first time inhibitors of Flt3ITD for treating for example 30 to 35% of patients with AML presenting this mutation.

Among our compounds, we also have found inhibitors of FGPR3 which is responsible for several lethal cancers.

Many different compounds have been described as tyrosine kinase inhibitors, for example, bis monocyclic, bicyclic or heterocyclic aryl compounds (WO 92/20642), vinylene-azaindole derivatives (WO 94/14808), 1-cyclopropyl-4-pyridyl-quinolones (U.S. Pat. No. 5,330,992), styryl compounds (U.S. Pat. No. 5,217,999), styryl-substituted pyridyl compounds (U.S. Pat. No. 5,302,606), selenoindoles and selenides (WO 94/03427), tricyclic polyhydroxylic compounds (WO 92/21660), benzylphosphonic acid compounds (WO 91/15495), pyrimidine derivatives (U.S. Pat. No. 5,521, 184 and WO 99/03854), indolinone derivatives and pyrrole-substituted indolinones (U.S. Pat. No. 5,792,783, EP 934 931, U.S. Pat. No. 5,834,504, U.S. Pat. No. 5,883,116, U.S. Pat. No. 5,883,113, U.S. Pat. No. 5,886,020, WO 96/40116 and WO 00/38519), as well as bis monocyclic, bicyclic aryl and heteroaryl compounds (EP 584 222, U.S. Pat. No. 5,656,643 and WO 92/20642), quinazoline derivatives (EP 602 851, EP 520 722, U.S. Pat. No. 3,772,295 and U.S. Pat. No. 4,343, 940) and aryl and heteroaryl quinazoline (U.S. Pat. No. 5,721, 237, U.S. Pat. No. 5,714,493, U.S. Pat. No. 5,710,158 and WO 95/15758).

There are hundreds of tyrosine kinases in mammalian cells that are more or less proned to be modulated by the compounds cited above. The problems is that a tyrosine kinase inhibitor has to be very specific to one or very few kinases to avoid toxicity and side effects on the long run. None of these prior art tyrosine kinase inhibitors provides a solution for this problem. Besides, none of these compounds have been described as potent and selective inhibitors of c-kit or of the c-kit pathway, nor highly specific bcr-abl, FGFR and/or Flt-3 inhibitors.

The present invention provides potent and selective compounds capable of inhibiting wild type and/or mutated c-kit, as well as subsets of compounds inhibiting c-kit, bcr-abl, FGFR3 and/or Flt-3.

In connection with the present invention, we have found that compounds corresponding to the 2-aminoaryloxazoles are potent and selective inhibitors of c-kit, bcr-abl, FGFR3 and/or Flt-3. These compounds are good candidates for treating diseases such as autoimmunes diseases, inflammatory diseases, cancers and mastocytosis. Compounds of the invention displaying inhibitory activity on Flt3 are particularly suitable for treating different forms of leukemia, such as AML. Compounds of the invention displaying inhibitory activity on FGFR3 constitute a breakthrough for treating lethal cancers such as bladder cancer, myeloma 414 and airways cancers.

DESCRIPTION

Therefore, the present invention relates to compounds belonging to the 2-aminoaryloxazoles. These compounds are capable of selectively inhibiting signal transduction involving the tyrosine phospholinase c-kit, bcr-abl, Flt-3 and mutant forms thereof.

In a first embodiment, the invention is aimed at compounds of formula I, which may represent either free base forms of the substances or pharmaceutically acceptable salts thereof:

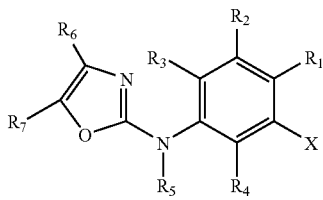

FORMULA I

Substituents R1-R7 and X in Formula I are defined as follows:

R1, R2, R3 and R4 each independently are selected from hydrogen, halogen (selected from F, Cl, Br or I), a linear or branched alkyl group containing from 1 to 10 carbon atoms and optionally substituted with one or more hetereoatoms such as halogen (selected from F, Cl, Br or I), oxygen, and nitrogen, the latter optionally in the form of a pendant basic nitrogen functionality; as well as trifluoromethyl, $C_{1-6}$alkyloxy, amino, $C_{1-6}$alkylamino, di($C_{1-6}$alkyl)amino, carboxyl, cyano, nitro, formyl, hydroxy, and CO—R, COO—R, CONH—R, SO2-R, and SO2NH—R wherein R is a linear or branched alkyl group containing from 1 to 10 carbon atoms and optionally substituted with at least one heteroatom, notably a halogen (selected from F, Cl, Br or I), oxygen, and nitrogen, the latter optionally in the form of a pendant basic nitrogen functionality.

R5 is one of the following:
(i) hydrogen, or
(ii) a linear or branched alkyl group containing from 1 to 10 carbon atoms and optionally substituted with one or more hetereoatoms such as halogen (selected from F, Cl, Br or I), oxygen, and nitrogen, the latter optionally in the form of a pendant basic nitrogen functionality, or
(iii) CO—R8 or COOR8 or CONHR8 or SO2R8 wherein R8 may be
  a linear or branched alkyl group containing from 1 to 10 carbon atoms and optionally substituted with one or more hetereoatoms such as halogen (selected from F, Cl, Br or I), oxygen, and nitrogen, the latter optionally in the form of a pendant basic nitrogen functionality, or
  an aryl group such as phenyl or a substituted variant thereof bearing any combination, at any one ring position, of one or more substituents such as halogen (selected from F, Cl, Br or I), alkyl groups containing from 1 to 10 carbon atoms and optionally substituted with one or more hetereoatoms such as halogen (selected from F, Cl, Br or I), oxygen, and nitrogen, the latter optionally in the form of a pendant basic nitrogen functionality, as well as trifluoromethyl, $C_{1-6}$alkyloxy, carboxyl, cyano, nitro, formyl, hydroxy, $C_{1-6}$alkylamino, di($C_{1-6}$alkyl)amino, and amino, the latter nitrogen substituents optionally in the form of a pendant basic nitrogen functionality, as well as CO—R, COO—R, CONH—R, SO2-R, and SO2NH—R wherein R is a linear or branched alkyl group containing from 1 to 10 carbon atoms and optionally substituted with at least one heteroatom, notably a halogen (selected from F, Cl, Br or I), oxygen, and nitrogen, the latter optionally in the form of a pendant basic nitrogen functionality, or
  a heteroaryl group such as a pyridyl, pyrimidinyl, pyrazinyl, pyridazinyl, thienyl, thiazolyl, imidazolyl, pyrazolyl, pyrrolyl, furanyl, oxazolyl, isoxazolyl, triazolyl, tetrazolyl, indolyl, benzimidazole, quinolinyl group, which may additionally bear any combination, at any one ring position, of one or more substituents such as halogen (selected from F, Cl, Br or I), alkyl groups containing from 1 to 10 carbon atoms and optionally substituted with one or more hetereoatoms such as halogen (selected from F, Cl, Br or I), oxygen, and nitrogen, the latter optionally in the form of a pendant basic nitrogen functionality as well as trifluoromethyl, $C_{1-6}$alkyloxy, carboxyl, cyano, nitro, formyl, hydroxy, $C_{1-6}$alkylamino, di($C_{1-6}$alkyl)amino, and amino, the latter nitrogen substituents optionally in the form of a basic nitrogen functionality; as well as CO—R, COO—R, CONH—R, SO2-R, and SO2NH—R wherein R is a linear or branched alkyl group containing from 1 to 10 carbon atoms and optionally substituted with at least one heteroatom, notably a halogen (selected from F, Cl, Br or I), oxygen, and nitrogen, the latter optionally in the form of a pendant basic nitrogen functionality.

R6 and R7 each independently are selected from:
i) hydrogen, a halogen (selected from F, Cl, Br or I), or
ii) an alkyl[1] group defined as a linear, branched or cycloalkyl group containing from 1 to 10 carbon atoms, or from 2 or 3 to 10 carbon atoms, (for example methyl, ethyl, propyl, butyl, pentyl, hexyl . . . ) and optionally substituted with one or more hetereoatoms such as halogen (selected from F, Cl, Br or I), oxygen, and nitrogen (the latter optionally in the form of a pendant basic nitrogen functionality); as well as trifluoromethyl, carboxyl, cyano, nitro, formyl; as well as CO—R, COO—R, CONH—R, SO2-R, and SO2NH—R wherein R is a linear or branched alkyl group containing 1 to 10 carbon atoms, or from 2 or 3 to 10 carbon atoms, (for example methyl, ethyl, propyl, butyl, pentyl, hexyl . . . ) and optionally substituted with at least one heteroatom, notably a halogen (selected from F, Cl, Br or I), oxygen, and nitrogen, the latter optionally in the form of a pendant basic nitrogen functionality); as well as a cycloalkyl or aryl[1] or heteroaryl[1] group optionally substituted by a pendant basic nitrogen functionality, or (iii) an aryl[1] group defined as phenyl or a substituted variant thereof bearing any combination, at any one ring position, of one or more substituents such as
  halogen (selected from I, F, Cl or Br);
  an alkyl[1] group;
  a cycloalkyl, aryl or heteroaryl group optionally substituted by a pendant basic nitrogen functionality;

trifluoromethyl, O-alkyl¹, carboxyl, cyano, nitro, formyl, hydroxy, NH-alkyl¹, N(alkyl¹)(alkyl¹), and amino, the latter nitrogen substituents optionally in the form of a basic nitrogen functionality, NHCO—R or NHCOO—R or NHCONH—R or NHSO2-R or NHSO2NH—R or CO—R or COO—R or CONH—R or SO2-R or SO2NH—R wherein R corresponds to hydrogen, alkyl¹, aryl or heteroaryl, or (iv) a heteroaryl¹ group defined as a pyridyl, pyrimidinyl, pyrazinyl, pyridazinyl, thienyl, thiazolyl, imidazolyl, pyrazolyl, pyrrolyl, furanyl, oxazolyl, isoxazolyl, triazolyl, tetrazolyl, indolyl, benzimidazole, quinolinyl group, which may additionally bear any combination, at any one ring position, of one or more substituents such as halogen (selected from F, Cl, Br or I);

an alkyl¹ group;

a cycloalkyl, aryl or heteroaryl group optionally substituted by a pendant basic nitrogen functionality, trifluoromethyl, O-alkyl¹, carboxyl, cyano, nitro, formyl, hydroxy, NH-alkyl¹, N(alkyl¹)(alkyl¹), and amino, the latter nitrogen substituents optionally in the form of a basic nitrogen functionality, NHCO—R or NHCOO—R or NHCONH—R or NHSO2-R or NHSO2NH—R or CO—R or COO—R or CONH—R or SO2-R or SO2NH—R wherein R corresponds to hydrogen, alkyl¹, or (v) an O-aryl¹, or NH-aryl¹, or O-heteroaryl¹ or NH-heteroaryl¹ group (vi) trifluoromethyl, O-alkyl¹, carboxyl, cyano, nitro, formyl, hydroxy, NH-alkyl¹, N(alkyl¹)(alkyl¹), and amino, the latter nitrogen substituents optionally in the form of a basic nitrogen functionality, or (vi) NHCO—R or NHCOO—R or NHCONH—R or NHSO2-R or NHSO2NH—R or CO—R or COO—R or CONH—R or SO2-R or SO2NH—R wherein R corresponds to hydrogen, alkyl¹, aryl or heteroaryl.

Substituent X is:

—NR9R10, wherein R9 and/or R10 are hydrogen or:

i) an alkyl¹ group, CF3 or ii) an aryl¹, heteroaryl¹ or cycloalkyl group optionally substituted by a pendant basic nitrogen functionality, or iii) a CO—R, COO—R, CON—RR' or SO2-R, where R and R' are a hydrogen, alkyl¹, aryl¹ or heteroaryl¹, optionally substituted by a pendant basic nitrogen functionality; or:

—CO—NR9R10, wherein R9 and/or R10 are hydrogen or:

i) an alkyl¹ group, CF3 or ii) an aryl¹, heteroaryl¹ or cycloalkyl group optionally substituted by a pendant basic nitrogen functionality, or X may also be Alkyl¹.

Among the particular compounds of formula I, the invention is directed to oxazol-2-yl-benzene-1,3-diamine compounds of the following formula I-2:

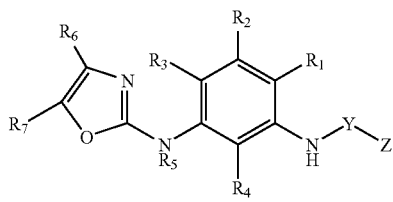

wherein R5=H, Y and Z represents an hydrogen, an aryl¹ or a heteroaryl¹ group, optionally substituted by a pendant basic nitrogen functionality. R1, R2, R3, R4, R6, and R7 have the meaning as depicted above.

An example of preferred compounds of the above formula is depicted below:

001: 4-{[4-Methyl-3-(4-pyridin-3-yl-oxazol-2-ylamino)-phenylamino]-methyl}-benzoic acid methyl ester

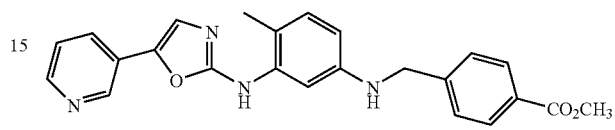

¹H NMR (CDCl₃, 300 MHz) δ=2.15 (s, 3H); 3.81 (s, 3H); 4.35 (s, 2H); 6.19 (d, J=6.0 Hz, 1H); 6.70 (br s, 1H); 6.90 (d, J=6.0 Hz, 1H); 7.23 (m, 1H); 7.38 (d, J=9.0, 2H); 7.41 (br s, 1H); 7.93 (d, J=9.0, 2H) 8.88 (br s, 1H); 8.42 (br s, 1H); 8.70 (br s, 1H).

014: 4-Methyl-N1-(5-pyridin-3-yl-oxazol-2-yl)-N3-(5-pyridin-4-yl-oxazol-2-yl)-benzene-1,3-diamine m. p. > 265° C.

015: 4-Methyl-N1-(5-phenyl-oxazol-2-yl)-N-3-(5-pyridin-4 yl-oxazol-2-yl)-benzene-1,3-diamine m. p. = 161° C.

016: 4-Methyl-N1-(5-phenyl-[1,3,4]oxadiazol-2-yl)-N3-(5-pyridin-4-yl-oxazol-2-yl)-benzene-1,3-diamine m. p. > 265° C.

017: N1-Benzooxazol-2-yl-4-methyl-N3-(5-pyridin-4-yl-oxazol-2-yl)-benzene-1,3-diamine

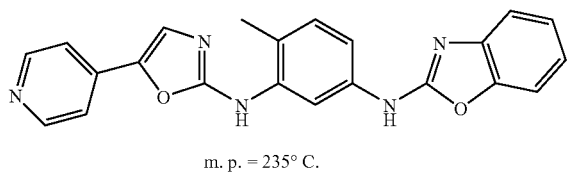

m. p. = 235° C.

Among the compounds of formula I, the invention is particularly embodied by the compounds wherein R5=H, X is NHSO2R group, R is independently alkyl[1], aryl[1] or heteroaryl[1]. corresponding to the family [3-(Oxazol-2-ylamino)-phenyl]-sulfonamide and the following formula I-3.

FORMULA I-3

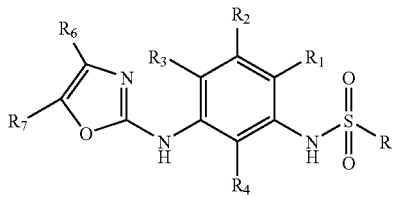

wherein R1, R2, R3, R4, R6 and R7 have the meaning as defined above in formula I.

EXAMPLES

057: N-[4-Methyl-3-(5-pyridin-4-yl-oxazol-2-ylamino)-phenyl]-C-phenyl-methanesulfon-amide

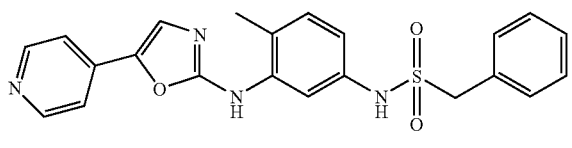

m. p. = 190-192° C.

Among the compounds of formula I, the invention is particularly embodied by the compounds of the following formula II:

FORMULA II

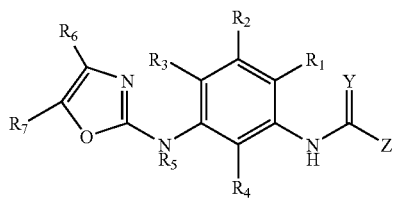

Wherein R5=H, Y is selected from O, S and Z corresponds to H, alkyl[1], or NRR', wherein R and R' are independently chosen from H or alkyl[1] or aryl[1] or heteroaryl[1], optionally substituted by a pendant basic nitrogen functionality. R1, R2, R3, R4, R6, and R7 have the meaning described above for formula I.

It also relates to compounds of formula II, wherein Y is selected from O, S and Z corresponds to H, NRaRb, alkyl[1], aryl[1], O-alkyl[1], or O-aryl[1] wherein Ra and Rb are independently chosen from H or alkyl[1] or aryl[1] or heteroaryl[1], optionally substituted by a pendant basic nitrogen functionality. R1, R2, R3, R4, R5, R6, and R7 have the meaning as depicted above for formula I.

EXAMPLES

002: N-[4-Methyl-3-(5-pyridin-3-yl-oxazol-2-ylamino)-phenyl]-acetamide

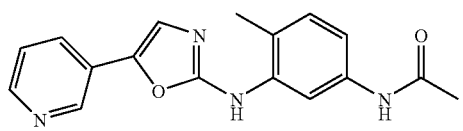

m. p. = 240-242° C.

018: 2-Cyano-N-[4-methyl-3-(5-pyridin-4-yl-oxazol-2-ylamino)-phenyl]-acetamide

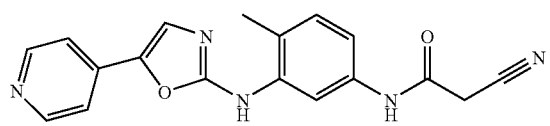

m. p. = 163° C.

019: 2-Ethoxy-N-[4-methyl-3-(5-pyridin-3-yl-oxazol-2-ylamino)-phenyl]-acetamide

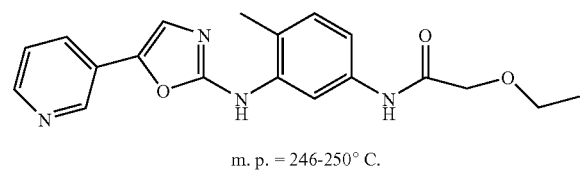

m. p. = 246-250° C.

020: 3-Methoxy-N-[4-methyl-3-(5-pyridin-3-yl-oxazol-2-ylamino)-phenyl]-propionamide

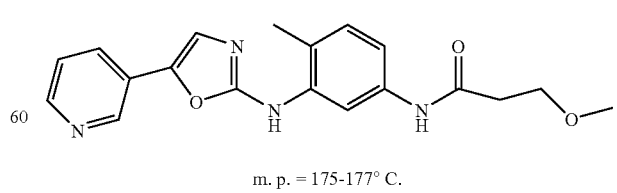

m. p. = 175-177° C.

Among the compounds of formula II, the invention is particularly embodied by the compounds wherein R5=H, Y=O or S, Z is a NRaRb group, corresponding to the [3-(oxazol-2- ylamino)-phenyl]-urea or the [3-(oxazol-2-ylamino)-phenyl]-thiourea family and the following formula II-1:

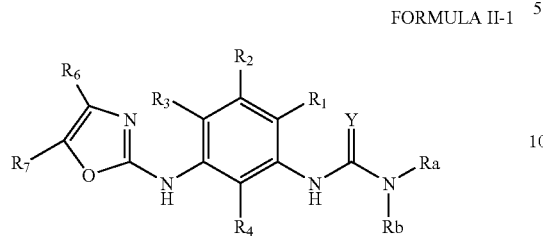

FORMULA II-1 wherein Ra, Rb are independently chosen from H or alkyl or aryl[1] or heteroaryl[1], optionally substituted by a pendant basic nitrogen functionality. R1, R2, R3, R4, R6, and R7 have the meaning described above.

EXAMPLES

003: 1-[4-Methyl-3-(5-pyridin-3-yl-oxazol-2-ylamino)-phenyl]-3-p-tolyl-urea

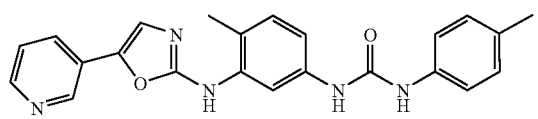

m. p. = 214° C.

004: 1-(4-Cyano-phenyl)-3-[4-methyl-3-(5-pyridin-3-yl-oxazol-2-ylamino)-phenyl]-urea

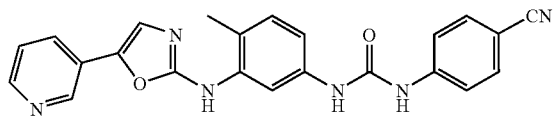

m. p. = 266° C.

005: 1-(4-Fluoro-phenyl)-3-[4-methyl-3-(5-pyridin-3-yl-oxazol-2-ylamino)-phenyl]-urea

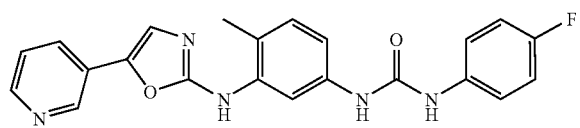

m. p. = 240° C.

006: 1-(2-Fluoro-phenyl)-3-[4-methyl-3-(5-pyridin-3-yl-oxazol-2-ylamino)-phenyl]-urea

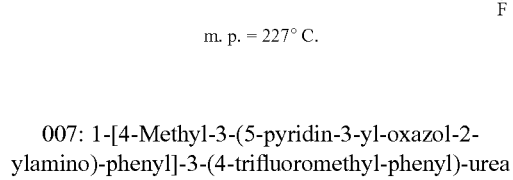

m. p. = 227° C.

007: 1-[4-Methyl-3-(5-pyridin-3-yl-oxazol-2-ylamino)-phenyl]-3-(4-trifluoromethyl-phenyl)-urea

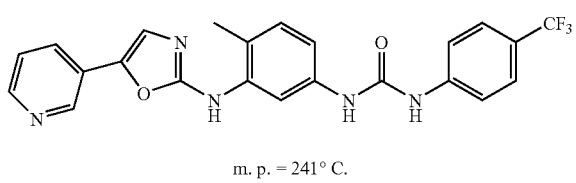

m. p. = 241° C.

008: 1-(4-Chloro-phenyl)-3-[4-methyl-3-(5-pyridin-3-yl-oxazol-2-ylamino)-phenyl]-urea

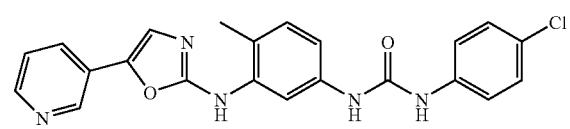

m. p. = 220° C.

021: 1-[4-Methyl-3-(5-phenyl-oxazol-2-ylamino)-phenyl]-3-(3-trifluoromethyl-phenyl)-urea

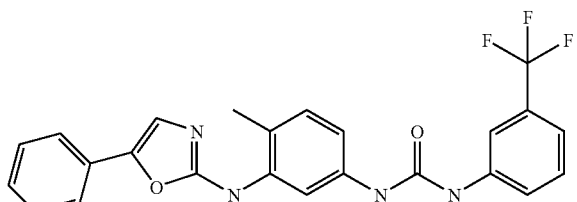

m. p. = 243° C.

022: 1-(4-Cyano-phenyl)-3-[4-methyl-3-(5-pyridin-3-yl-oxazol-2-ylamino)-phenyl]-thiourea

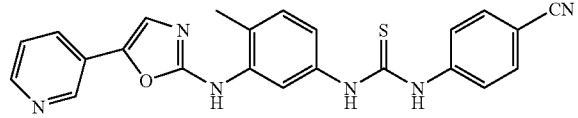

m. p. = 205° C.

023: 1-(4-Cyano-phenyl)-3-[4-methyl-3-(5-pyridin-4-yl-oxazol-2-ylamino)-phenyl]-thiourea

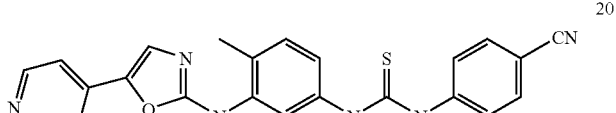

m. p. = 169-171° C.

024: (2-{2-Methyl-5-[3-(4-trifluoromethyl-phenyl)-ureido]-phenylamino}-oxazol-5-yl)-acetic acid ethyl ester

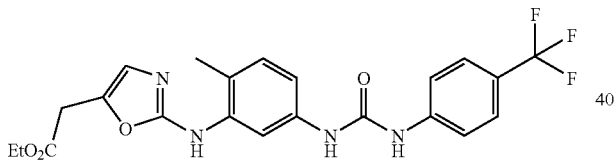

m. p. = 185° C.

025: 1-Benzyl-3-[4-methyl-3-(5-pyridin-4-yl-oxazol-2-ylamino)-phenyl]-thiourea

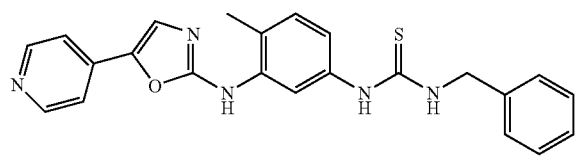

m. p. = 219° C.

Among the compounds of formula II, the invention is particularly embodied by the compounds wherein R5=H, Y is an oxygen and Z is an aryl$^1$ group, corresponding to the N-[3-(Oxazol-2-ylamino)-phenyl]-amide family and the following formula II-2:

FORMULA II-2

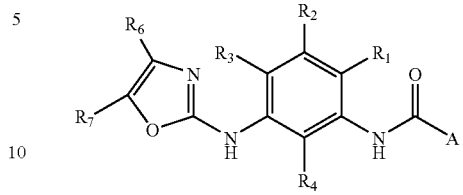

Wherein A is aryl$^1$ or heteroaryl$^1$ and
wherein R1, R2, R3, R4, R6, R7, aryl$^1$, heteroaryl$^1$ have the meaning described on pages as defined in formula I.

EXAMPLES

009: 4-(4-Methyl-piperazin-1-ylmethyl)-N-[4-methyl-3-(5-pyridin-3-yl-oxazol-2-ylamino)-phenyl]-benzamide

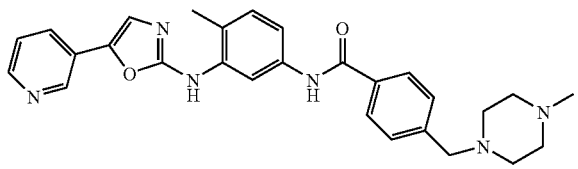

m. p. = 218° C.

010: 3-Dimethylamino-N-[4-methyl-3-(5-pyridin-3-yl-oxazol-2-ylamino)-phenyl]-benzamide

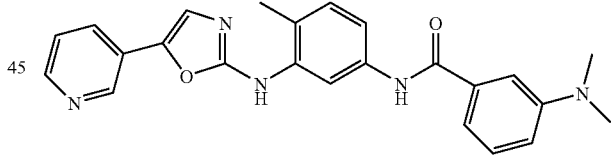

m. p. = 215° C.

011: 3-Bromo-N-[4-methyl-3-(5-pyridin-3-yl-oxazol-2-ylamino)-phenyl]-benzamide

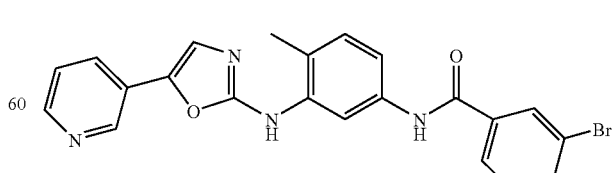

m. p. = 244° C.

026: N-[4-Methoxy-3-(5-pyridin-3-yl-oxazol-2-ylamino)-phenyl]-3-trifluoromethyl-benzamide

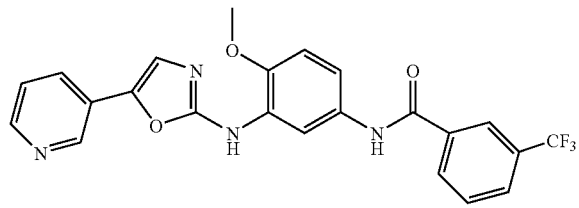

m. p. = 229° C.

027: 4-(3-Dimethylamino-propylamino)-N-[4-methyl-3-(5-pyridin-3-yl-oxazol-2-ylamino)-phenyl]-3-trifluoromethyl-benzamide

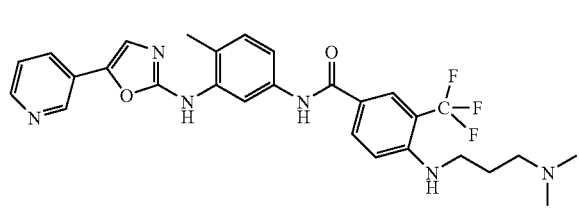

m. p. = 247° C.

028: N-[4-Fluoro-3-(5-pyridin-3-yl-oxazol-2-ylamino)-phenyl]-3-trifluoromethyl-benzamide

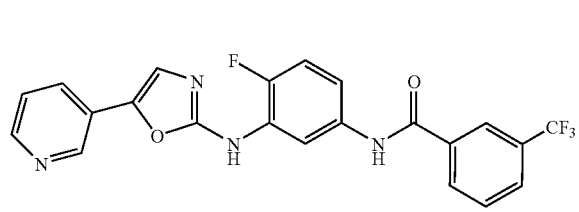

m. p. > 265° C.

029: 1H-Indole-6-carboxylic acid [4-methyl-3-(5-pyridin-4-yl-oxazol-2-ylamino)-phenyl]-amide

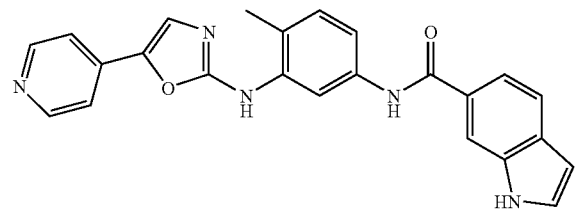

m. p. = 230-240° C.

030: 3-Isopropoxy-N-[4-methyl-3-(5-pyridin-4-yl-oxazol-2-ylamino)-phenyl]-benzamide

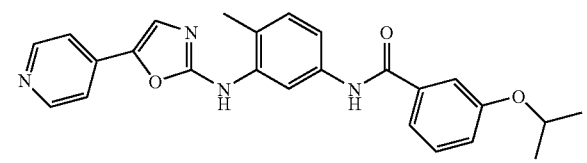

m. p. = 179-181° C.

031: N-[4Methyl-3-(5-pyridin-2-yl-oxazol-2-ylamino)-phenyl]-3-trifluoromethyl-benzamide

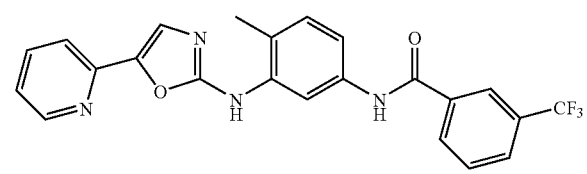

m. p. = 259° C.

032: 3,5-Dimethoxy-N-[4-methyl-3-(5-pyridin-4-yl-oxazol-2-ylamino)-phenyl]-benzamide

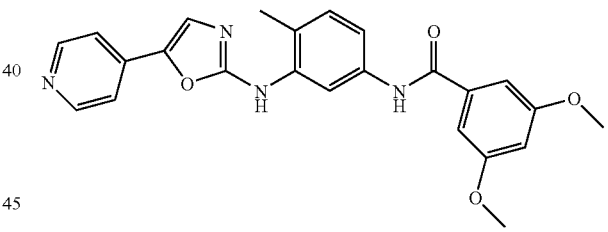

m. p. = 209° C.

033: N-[3-(5-Pyridin-3-yl-oxazol-2-ylamino)-phenyl]-3-trifluoromethyl-benzamide

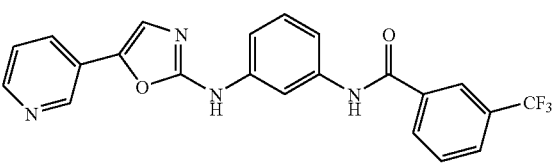

m. p. > 265° C.

034: N-[4-Methyl-3-(5-phenyl-oxazol-2-ylamino)-phenyl]-3-trifluoromethyl-benzamide

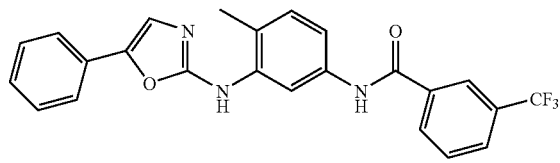

m. p.= 212° C.

035: 3-Fluoro-4-(4-methyl-piperazin-1-ylmethyl)-N-[4-methyl-3-(5-pyridin-3-yl-oxazol-2-ylamino)-phenyl]-benzamide

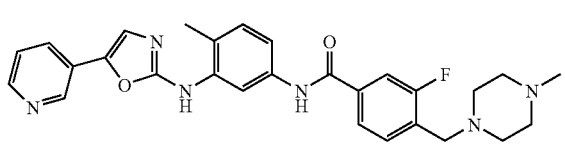

m.p. = 209° C.

036: N-[4-Chloro-3-(5-pyridin-3-yl-oxazol-2-ylamino)-phenyl]-3-trifluoromethyl-benzamide

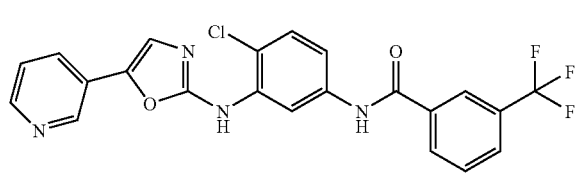

m. p. = 206° C.

037: N-[4-Methyl-3-(5-pyridin-3-yl-oxazol-2-ylamino)-phenyl]-terephthalamide

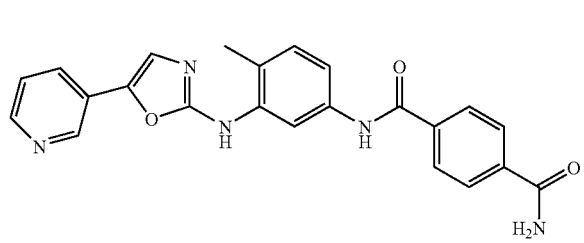

m. p. > 265° C.

038: 5-Methyl-isoxazole-4-carboxylic acid [4-methyl-3-(5-pyridin-4-yl-oxazol-2-ylamino)-phenyl]-amide

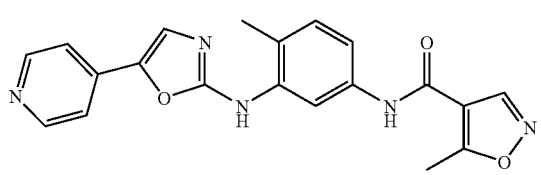

m.p. = 218° C.

039: 4-Cyano-N-[4-methyl-3-(5-pyridin-4-yl-oxazol-2-ylamino)-phenyl]-benzamide

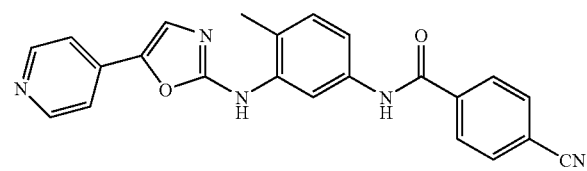

m. p. > 265° C.

040: N-[4-Methyl-3-(5-pyridin-3-yl-oxazol-2-ylamino)-phenyl]-isonicotinamide

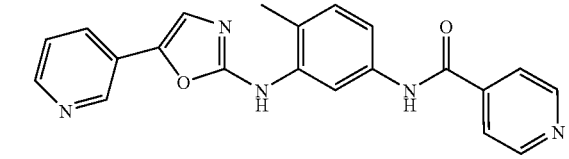

m. p. = 249° C.

041: N-[4-Methyl-3-(4-pyridin-3-yl-oxazol-2-ylamino)-phenyl]-3-trifluoromethyl-benzamide

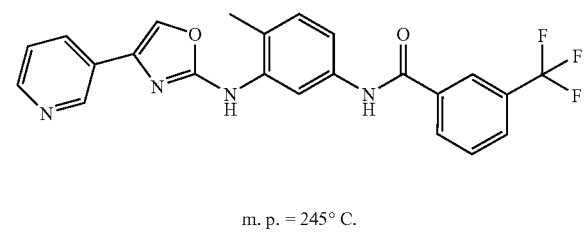

m. p. = 245° C.

Among the compounds of formula II, the invention is particularly embodied by the compounds wherein Y=O and Z a OR group, corresponding to the family [3-(Oxazol-2-ylamino)-phenyl]-carbamate and the following formula II-3.

FORMULA II-3

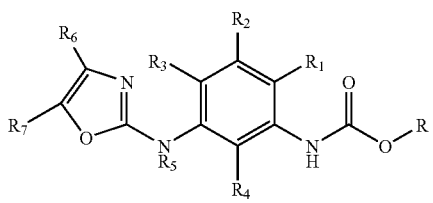

wherein R is independently alkyl$^1$, aryl$^1$ or heteroaryl$^1$. R1, R2, R3, R4, R5, R6, and R7 have the meaning described above for formula I.

EXAMPLES

012: [4-Methyl-3-(5-pyridin-3-yl-oxazol-2-ylamino)-phenyl]-carbamic acid isobutyl ester

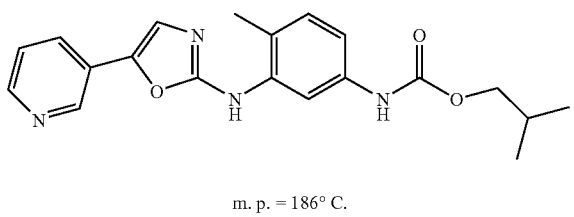

m. p. = 186° C.

013: (5-Isobutoxycarbonylamino-2-methyl-phenyl)-(5-pyridin-3-yl-oxazol-2-yl)-carbamic acid isobutyl ester

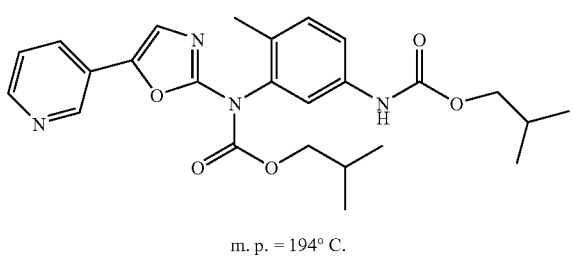

m. p. = 194° C.

42: [4-Methyl-3-(5-pyridin-4-yl-oxazol-2-ylamino)-phenyl]-carbamic acid isobutyl ester

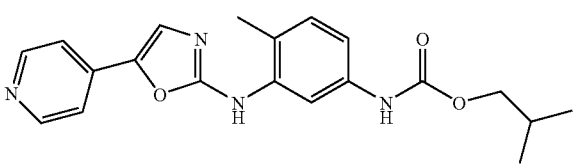

m. p. = 170° C.

Among the compounds of formula II, the invention is particularly embodied by the compounds wherein R5=H, Y is an oxygen and Z an alkyl$^1$ group, corresponding to the family [3-(Oxazol-2-ylamino)-phenyl]-acetamide and the following formula II-4.

FORMULA II-4

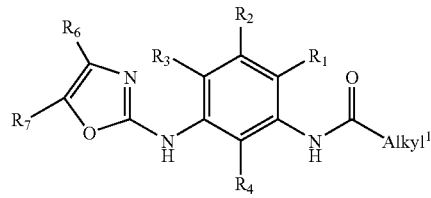

R1, R2, R3, R4, R6, R7 and alkyl$^1$ have the meaning as defined above.

EXAMPLES

043: N-[4-Methyl-3-(5-pyridin-4-yl-oxazol-2-ylamino)-phenyl]-2-m-tolyl-acetamide

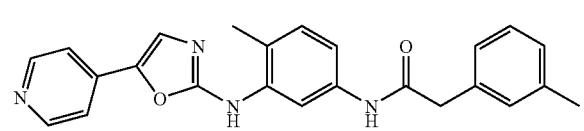

m. p. = 212° C.

044: 2-(4-Fluoro-phenyl)-N-[4-methoxy-3-(5-pyridin-4-yl-oxazol-2-ylamino)-phenyl]-acetamide

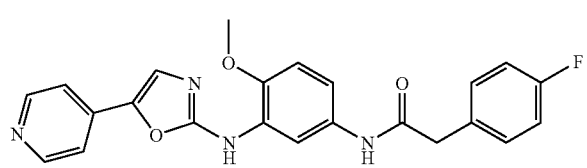

m. p. = 222° C.

045: 2-(2,4-Difluoro-phenyl)-N-[4-methyl-3-(5-phenyl-oxazol-2-ylamino)-phenyl]-acetamide

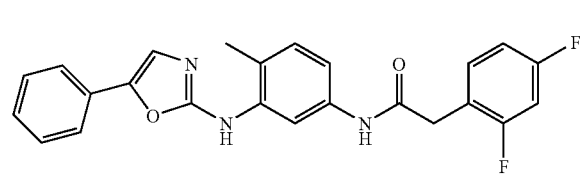

m. p. = 230° C.

046: 2-(3-Bromo-phenyl)-N-[4-methyl-3-(5-pyridin-2-yl-oxazol-2-ylamino)-phenyl]-acetamide

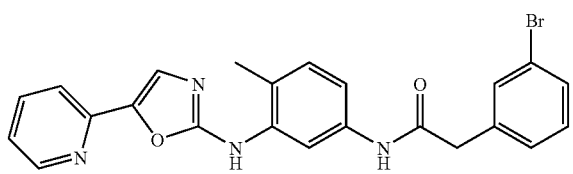

m. p. = 211° C.

047: 3-(4-Fluoro-phenyl)-N-[4-methyl-3-(5-pyridin-4-yl-oxazol-2-ylamino)-phenyl]-propionamide

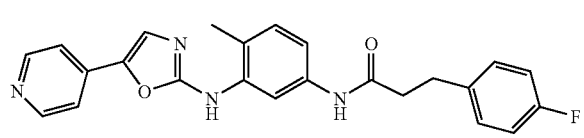

m. p. = 224° C.

048: 2-(4-Fluoro-phenyl)-N-[4-methyl-3-(5-pyridin-3-yl-oxazol-2-ylamino)-phenyl]-acetamide

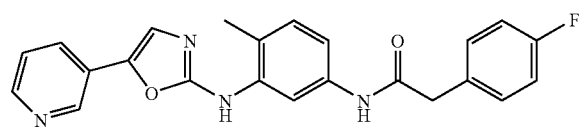

m. p. = 231-233° C.

049: N-{3-[5-(4-Cyano-phenyl)-oxazol-2-ylamino]-4-methyl-phenyl}-2-(2,4-difluoro-phenyl)-acetamide

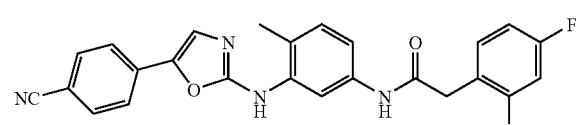

m. p. = 240° C.

050: 4-Methyl-pentanoic acid [4-methyl-3-(5-pyridin-3-yl-oxazol-2-ylamino)-phenyl]-amide

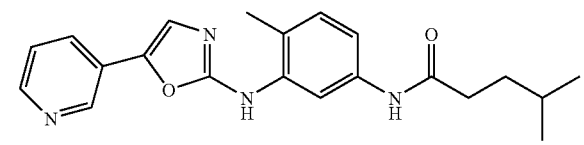

m. p. = 211° C.

051: N-[4-Methyl-3-(5-pyridin-3-yl-oxazol-2-ylamino)-phenyl]-2-piperazin-1-yl-acetamide

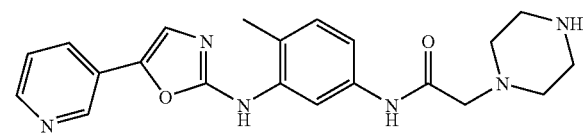

m. p. = 176-178° C.

052: N-[4-Methyl-3-(5-pyridin-3-yl-oxazol-2-ylamino)-phenyl]-3-piperazin-1-yl-propionamide

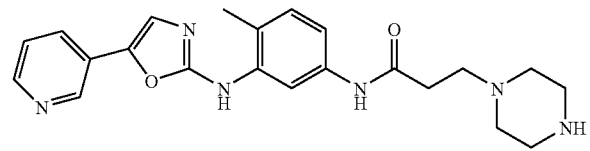

m. p. = 118-120° C.

053: 2-(2,6-Dichloro-phenyl)-N-[4-methyl-3-(5-pyridin-4-yl-oxazol-2-ylamino)-phenyl]-acetamide

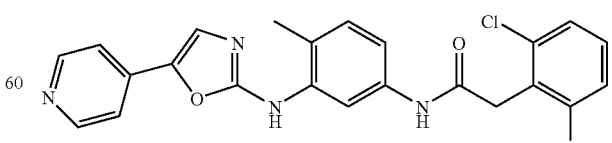

m. p. > 265° C.

054: N-[4-Methyl-3-(5-pyridin-3-yl-oxazol-2-ylamino)-phenyl]-3-pyrrolidin-1-yl-propionamide

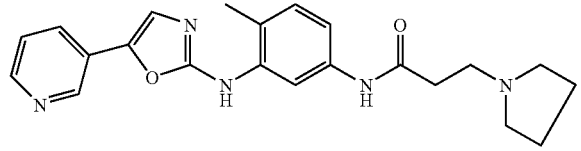

m. p. = 186° C.

055: N-[4-Methoxy-3-(5-pyridin-4-yl-oxazol-2-ylamino)-phenyl]-2-(4-trifluoromethyl-phenyl)-acetamide

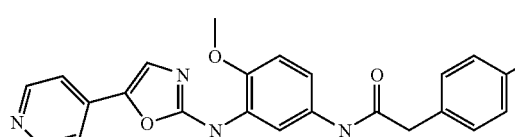

m. p. = 225° C.

056: 2-(4-Methoxy-phenyl)-N-[4-methyl-3-(5-pyridin-4-yl-oxazol-2-ylamino)-phenyl]-acetamide

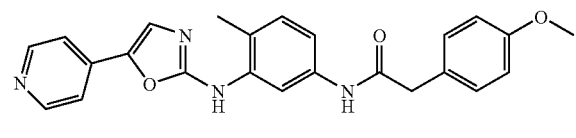

m. p. = 187° C.

Among the compounds of formula I, the invention is particularly embodied by the compounds of the following formula III:

FORMULA III

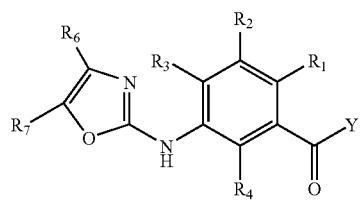

Wherein Y is selected from $NR_aR_b$, $NHNR_aR_b$, $alkyl^1$, $aryl^1$, or $O-R_a$ wherein $R_a$ and $R_b$ are independently chosen from H or $alkyl^1$ or $aryl^1$ or $heteroaryl^1$, optionally substituted by a pendant basic nitrogen functionality. R1, R2, R3, R4, R6, and R7 have the meaning described above for formula I.

EXAMPLES

058: N-(4-Cyano-phenyl)-4-methyl-3-(5-pyridin-3-yl-oxazol-2-ylamino)-benzamide

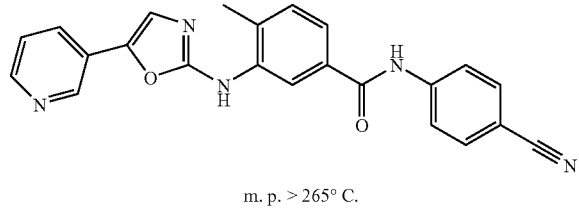

m. p. > 265° C.

059: N-(3-Dimethylamino-phenyl)-4-methyl-3-(5-pyridin-4-yl-oxazol-2-ylamino)-benzamide

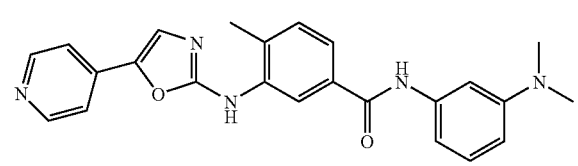

m.p. = 230° C.

060: N-(2-Dimethylamino-ethyl)-4-methyl-3-(5-pyridin-3-yl-oxazol-2-ylamino)-benzamide

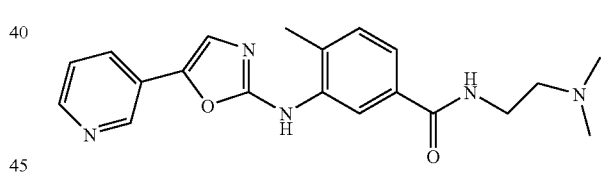

$^1$H NMR (CDCl$_3$, 300 MHz) δ 2.21 (s, 6H); 2.33 (s, 3H); 2.48 (t, J=5.9 Hz, 2H); 3.47 (q, J=5.6 Hz, 2H); 6.82 (s, 1H); 6.93 (s, 1H); 7.20 (m, 2H); 7.25 (m, 1H); 7.40 (dd, J=7.6-1.5 Hz, 1H); 7.74 (dt, J=8.0-1.8 Hz, 1H); 8.41 (dd, J=6.9-1.3 Hz, 2H); 8.76 (d, J=1.8, 1H).

061: N-(3-Fluoro-4-methyl-phenyl)-4-methyl-3-(5-pyridin-4-yl-oxazol-2-ylamino)-benzamide

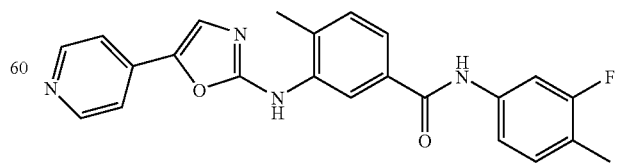

m. p. = 203° C.

062: N-(3-Chloro-phenyl)-4-methyl-3-(5-pyridin-3-yl-oxazol-2-ylamino)-benzamide

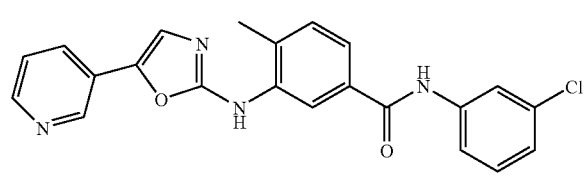

m. p. = 247° C.

063: N-Benzyl-4-methyl-3-(5-pyridin-4-yl-oxazol-2-ylamino)-benzamide

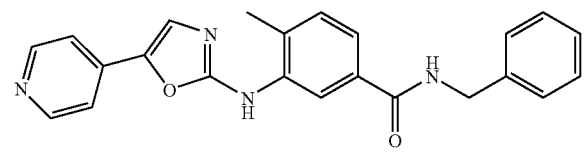

m. p. = 212° C.

064: N-(4-Methoxy-benzyl)-4-methyl-3-(5-pyridin-4-yl-oxazol-2-ylamino)-benzamide

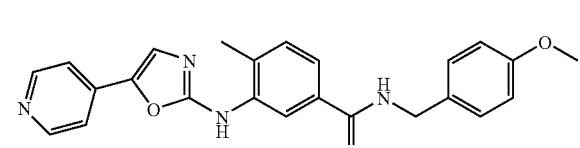

m. p. = 212-214° C.

065: [4-Methyl-3-(5-pyridin-4-yl-oxazol-2-ylamino)-phenyl]-morpholin-4-yl-methanone

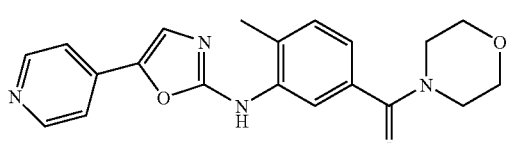

m. p. = 155° C.

066: [4-Methyl-3-(5-pyridin-4-yl-oxazol-2-ylamino)-phenyl]-piperazin-1-yl-methanone

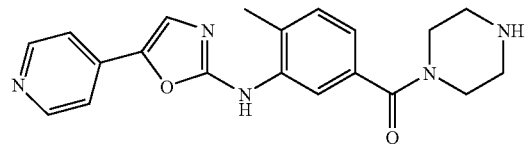

m. p. = 171° C.

Among the compounds of formula I, the invention is particularly embodied by the compounds of the following formula IV:

FORMULA IV

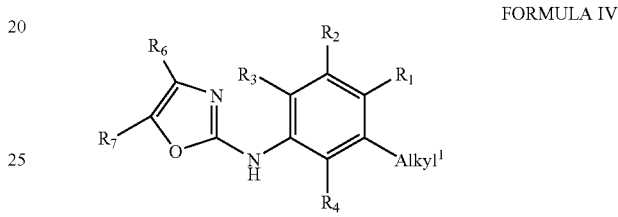

Wherein alkyl$^1$, R, R2, R3, R4, R6, and R7 have the meaning as defined for formula I above.

EXAMPLES

067: N-(4-Fluoro-phenyl)-2-[4-methyl-3-(5-pyridin-4-yl-oxazol-2-ylamino)-phenyl]-acetamide

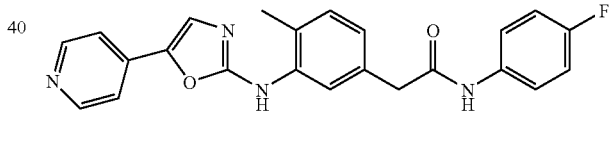

m. p. = 220-222° C.

Among the compounds as described above of formula I-2, I-3, II, II-2, II-3, II-4, III and IV, the invention contemplates more particularly the groups wherein R6 is hydrogen and R7 is pyridyl; which pyridyl may additionally bear any combination, at any one ring position, of one, two or three or four substituents such as halogen (selected from F, Cl, Br or I);

an alkyl$^1$ group;

an aryl$^1$ group;

trifluoromethyl, O-alkyl$^1$, carboxyl, cyano, nitro, formyl, hydroxy, NH-alkyl$^1$, N(alkyl$^1$)(alkyl$^1$), and amino, the latter nitrogen substituents optionally in the form of a basic nitrogen functionality, NHCO—R or NHCOO—R or NHCONH—R or NHSO2-R or NHSO2NH—R or CO—R or COO—R or CONH—R or SO$_2$—R or SO2NH—R wherein R corresponds to hydrogen, alkyl$^1$ or aryl$^1$ group.

In a second embodiment, the invention is directed to a process for manufacturing a compound of formula I depicted above. This entails the condensation of an azide of general formula 10 with an isocyanate of the type 11 or an isothiocyanate of the type 12.

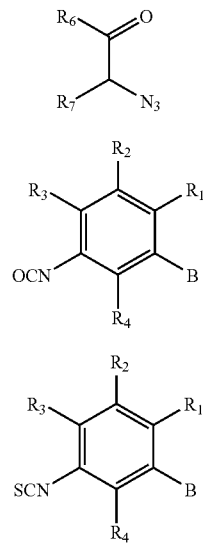

Group B in formula 11 and 12 corresponds to group X as described in formula I as well as NO2, CO2, and CH3. R1, R2, R3, R4, R6 and R7 have the meaning described above for formula I.

The reaction of 10 either with 11 or 12 in a solvent such as methylene chloride or dioxane in the presence of triphenylphosphine, leads to an oxazole-type product of formula 13.

The following examples are intended to illustrate the present invention

EXAMPLE OF COMPOUND SYNTHESIS

General: All chemicals used were commercial reagent grade products. Solvents were of anhydrous commercial grade and were used without further purification. Dichloromethane and dioxane were freshly distilled under a stream of argon before use. The progress of the reactions was monitored by thin layer chromatography using precoated silica gel 60F 254, Merck TLC plates, which were visualized under UV light. Multiplicities in $^1$H NMR spectra are indicated as singlet (s), broad singlet (br s), doublet (d), triplet (t), quadruplet (q), and multiplet (m) and the NMR spectrum were realized on a 300 MHz Bruker spectrometer.

Preparation of 3-Bromoacetylpyridine, HBr Salt

Bromine (24 g, 150 mmol) in 4 mL of 45% HBr was added dropwise under vigorous stirring to a solution at 70° C. of 3-acetyl-pyridine (18 g, 148 mmol) in acetic acid containing 45% of HBr (165 mL). The vigorously stirred mixture was keep at 70° C. for 3 h. The mixture was cooled and the precipitate collected by filtration and washed with petroleum ether/methanol (1/1, 100 mL) to give 35.8 g of a white crystals (85%).

m.p. 189° C. $^1$H NMR (DMSO-d6) δ=5.09 (s, 2H, CH$_2$Br); 7.78-7.96 (m, 1H, pyridyl-H); 8.42-8.70 (m, 1H, pyridyl-H); 8.79-8.99 (m, 1H, pyridyl-H); 9.29 (m, 1H, pyridyl-H); 12.77 (br s, 1H, HBr)

Preparation of 3-Azidoacetylpyridine

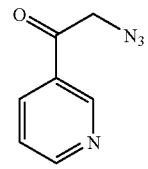

To a solution of 3-bromoacetylpyridine hydrobromide (5 g, 17.8 mmol) in 20 mL of water was added sodium azide (1.16 g, 17.8 mmol) and the contents stirred at room temperature for 2 h. The reaction mixture was treated with saturated aqueous NaHCO$_3$ until neutrality, extracted with ethyl acetate (3×30 mL) and the combined organic phases were dried over MgSO$_4$. After solvent removal the crude residue was silica gel column chromatographed (dichloromethane/ethanol/98/2). 3-Azidoacetyl-pyridine was obtained as yellow solid (2.17 g, 71%).

m.p.=69-71° C. $^1$H NMR (CDCl$_3$) δ=4.50 (s, 2H, CH$_2$N$_3$); 7.38 (dd, J=7.9-4.9, 1H, pyridyl-H); 8.11 (d, J=7.9, 1H, pyridyl-H); 8.71 (d, J=7.9, 1H, pyridyl-H); 8.99 (s, 1H, pyridyl-H).

Preparation of (2-Methyl-5-nitro-phenyl)-(5-pyridin-3-yl-oxazol-2-yl)-amine

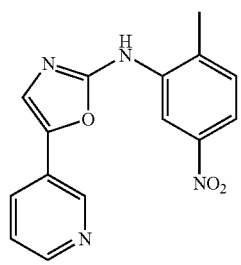

To a solution of 3-azidoacetylpyridine (800 mg, 4.94 mmol) in dioxane 10 mL was added 2-methyl-5-nitrophenyl isocyanate (880 mg, 4.94 mmol) (commercially available), and triphenylphosphine (1.29 g, 4.94 mmol). The reaction mixture was placed in an oil bath preheated to 100° C. and stirred for 30 min. After evaporation of the solvent under reduced pressure the residue was partitioned between 4N HCl (20 mL) and dichloromethane (20 mL). The aqueous layer was neutralized with 15% NaOH and extracted with dichloromethane (3×20 mL). The combined organic layers were washed with brine (20 mL), dried over anhydrous MgSO$_4$, concentrated. The residue was silica gel column chromatographed (dichloromethane/ethanol:97/3) to give the title compound as yellow micro crystals (1.14 g, 78%).

m.p.=252° C. $^1$H NMR (DMSO-d$^6$) δ=2.46 (s, 3H, ArCH$_3$); 7.47-7.50 (m, 2H); 7.71 (s, 1H); 7.81 (dd, J=8.2-2.4,

1H); 7.98 (d, J=7.6, 1H); 8.48 (d, J=4.6, 1H); 8.88 (br s, 1H); 9.07 (br s, 1H); 9.62 (s, 1H, NH).

Preparation of (2-Methyl-5-amino-phenyl)-(5-pyridin-3-yl-oxazol-2-yl)-amine

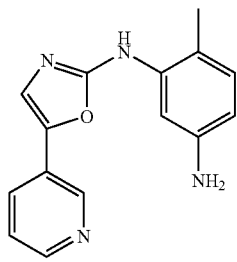

To a solution of (2-methyl-5-nitro-phenyl)-(5-pyridin-3-yl-oxazol-2-yl)-amine (600 mg, 2.02 mmol) in ethanol (20 mL) was added tin(II) chloride dihydrate (2.50 g, 10 mmol). The reaction mixture was heated under reflux for 6 h. The mixture was then concentrated, saturated aqueous NaHCO$_3$ was added and the resultant suspension was extracted with ethyl acetate (3×20 mL). The combined organic layers were washed with brine (20 mL), dried over anhydrous MgSO$_4$ and concentrated. The residue was silica gel column chromatographed (dichloromethane/ethanol:97/3). 350 mg (65%) of (2-methyl-5-amino-phenyl)-(5-pyridin-3-yl-oxazol-2-yl)-amine was obtained as pale yellow powder.

m.p.=166° C. $^1$H NMR (CDCl$_3$) δ=2.17 (s, 3H, ArCH$_3$); 6.28-6.31 (m, 1H); 6.63 (br s, 1H); 6.90 (d, J=8.1, 1H); 7.18 (s, 1H); 7.24 (dd, J=8.0-5.0, 1H); 7.44 (d, J=2.1, 1H); 7.72-7.75 (m, 1H); 8.41-8.43 (m, 1H); 8.76 (br s, 1H).

Preparation of 3-Dimethylamino-N-[4-methyl-3-(5-pyridin-3-yl-oxazol-2-ylamino)-phenyl]-benzamide

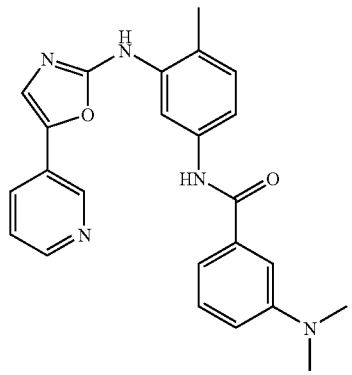

To a solution of (2-methyl-5-amino-phenyl)-(5-pyridin-3-yl-oxazol-2-yl)-amine (120 mg, 0.451 mmol) and 3-dimethylaminobenzoic acid (86 mg, 0.521 mmol) in DMF (6 mL) was added 1-(3-dimethylaminopropyl)-3-ethylcarbodiimide hydrochloride (136 mg, 0.824 mmol), 1-hydroxybenzotriazole (84 mg, 0.622 mmol) and triethylamine (0.98 ml, 0.710 mmol). The mixture was stirred at room temperature for 4 h. After removal of the solvent, the residue was treated with saturated aqueous NaHCO$_3$ (20 mL) and extracted with dichloromethane (3×10 mL). The combined organic layers were washed with brine (20 mL), dried over MgSO$_4$ and concentrated. 3-dimethylamino-N-[4-methyl-3-(5-pyridin-3-yl-oxazol-2-ylamino)-phenyl]-benzamide was obtained after silica gel column chromatography (dichloromethane/ethanol:98/2) (113 mg, 58%) as yellow solid.

m.p.=228° C. $^1$H NMR (DMSO-d$^6$) δ=2.27 (s, 3H, ArCH$_3$); 2.96 (s, 6H, 2×NCH$_3$); 6.90 (d, J=8.0, 1H); 7.14-7.33 (m, 4H); 7.40-7.46 (m, 2H); 7.57 (s, 1H); 7.95 (d, J=8.0, 1H); 8.23 (br s, 1H); 8.43 (d, J=4.7, 1H); 8.83 (br s, 1H); 9.39 (s, 1H); 10.04 (s, 1H).

Preparation of [4-Methyl-3-(5-pyridin-3-yl-oxazol-2-ylamino)-phenyl]-carbamic acid isobutyl ester

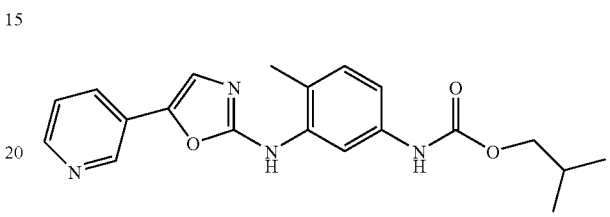

The (2-methyl-5-amino-phenyl)-(5-pyridin-3-yl-oxazol-2-yl)-amine (170 mg, 0.639 mmol) was dissolved in dry THF (7 mL) under argon atmosphere and Chloroformiate isobutyl (1.1 eq.) was added dropwise at 0° C. The reaction mixture was brought to room temperature and stirred for 3 h. Evaporation to drynes gave a solid residue which was purified by alumina gel column chromatography (dichloromethane/ethanol:98/2) to give white solid (62%).

m.p.=186° C. $^1$H NMR (DMSO-d$^6$) δ=0.93 (d, J=6.2, 6H); 1.92 (m, 1H); 2.21 (s, 3H); 3.86 (d, J=6.2, 2H); 7.10 (s, 2H); 7.44 (br s, 1H); 7.57 (s, 1H); 7.95 (s, 1H); 8.44 (s, 2H); 8.85 (s, 1H); 9.35 (s, 1H); 9.57 (s, 1H).

Preparation of N-(4-Cyano-phenyl)-4-methyl-3-(5-pyridin-3-yl-oxazol-2-ylamino)-benzamide

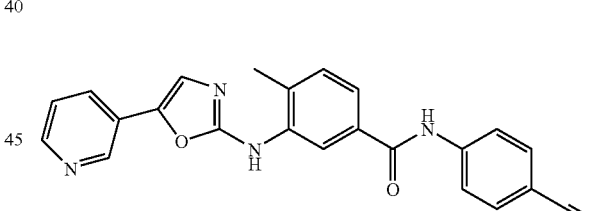

A 2M solution of trimethyl aluminium in hexanes (4 mL) was added dropwise to a cold (0° C.) solution of 4-aminobenzonitrile (236 mg, 2 mmol) in anhydrous dichloromethane (20 mL) under argon atmosphere. The mixture was warmed to room temperature and stirred at room temperature for 3 h. A solution of 4-methyl-3-(5-pyridin-4-yl-oxazol-2-ylamino)-benzoic acid methyl ester (620 mg, 2 mmol) in anhydrous dichloromethane (5 mL) and added slowly, and the resulting mixture was heated at reflux for 12 h. The mixture was cooled to 0° C. and quenched by dropwise addition of a 4N aqueous sodium hydroxide solution (10 mL). The mixture was extracted with dichloromethane (3×30 mL). The combined organic layers were washed with brine (3×40 mL) and dried over anhydrous MgSO$_4$. N-(4-cyano-phenyl)-4-methyl-3-(5-pyridin-3-yl-oxazol-2-ylamino)-benzamide is obtained in 78% after purification by silica gel column chromatography (dichloromethane/ethanol:98/2).

m.p.=203° C. $^1$H NMR (DMSO-d$^6$) δ=2.39 (s, 3H); 7.39 (d, J=8.0, 1H); 7.46 (m, 1H); 7.61 (s, 1H); 7.64 (s, 1H); 7.82 (d, J=8.6, 2H); 7.95 (d, J=8.1, 1H); 7.99 (d, J=8.6, 2H); 8.45 (s, 1H); 8.48 (s, 1H); 8.84 (s, 1H); 9.61 (s, 1H); 10.59 (s, 1H).

Preparation of N-[4-Methyl-3-(5-pyridin-3-yl-oxazol-2-ylamino)-phenyl]-2-piperazin-1-yl-acetamide

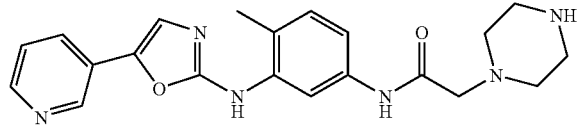

The (2-methyl-5-amino-phenyl)-(5-pyridin-3-yl-oxazol-2-yl)-amine (500 mg, 1.88 mmol) was dissolved in acetone (200 mL) under an argon atmosphere. K$_2$CO$_3$ (1.2 eq) was added and the suspension was cooled to 0° C. The chloroacetyl chloride (1.2 eq) was added dropwise and the mixture was brought to room temperature under stirring for 10 h. The resulting yellow suspension was filtered and K$_2$CO$_3$ was washed with methanol. The resulting organic solution was evaporated to dryness. The expected product was taken up from Et$_2$O to give a yellow powder (90%). To this chloroderivative (200 mg, 0.583 mmol) dissolved in absolute ethanol was added NaI (0.7 eq). The reaction mixture was heated to reflux and piperazine (12 eq) was added. The mixture was stirred for 10 h at reflux temperature. The solution was then diluted with dichloromethane and washed with an aqueous saturated solution of NaHCO$_3$. The aqueous layer was extracted with dichloromethane (3×25 ml). The combined extracts were dried over MgSO$_4$, filtered and concentrated under reduced pressure to dryness. A column chromatography on alumina (dichloromethane/ethanol:98/2) provided the expected product as a beige solid (70%).

m.p.=176-178° C. $^1$H NMR (CDCl$_3$) δ=3.73 (s, 3H); 4.15 (br s, 4H); 4.50 (br s, 4H); 4.68 (s, 2H); 8.61 (d, J=8.3, 1H); 8.78 (d, J=7.2, 1H); 8.93 (m, 1H); 9.06 (s, 1H); 9.43 (d, J=7.8, 1H); 9.58 (s, 1H); 9.93 (dd, J=4.6-1.2, 1H); 10.33 (s, 1H); 10.87 (s, 1H); 11.22 (s, 1H).

In a third embodiment, the invention relates to a pharmaceutical composition comprising a compound as depicted above.

Such medicament can take the form of a pharmaceutical composition adapted for oral administration, which can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The composition of the invention can also take the form of a pharmaceutical or cosmetic composition for topical administration.

Such compositions may be presented in the form of a gel, paste, ointment, cream, lotion, liquid suspension aqueous, aqueous-alcoholic or, oily solutions, or dispersions of the lotion or serum type, or anhydrous or lipophilic gels, or emulsions of liquid or semi-solid consistency of the milk type, obtained by dispersing a fatty phase in an aqueous phase or vice versa, or of suspensions or emulsions of soft, semi-solid consistency of the cream or gel type, or alternatively of microemulsions, of microcapsules, of microparticles or of vesicular dispersions to the ionic and/or nonionic type. These compositions are prepared according to standard methods.

The composition according to the invention comprises any ingredient commonly used in dermatology and cosmetic. It may comprise at least one ingredient selected from hydrophilic or lipophilic gelling agents, hydrophilic or lipophilic active agents, preservatives, emollients, viscosity enhancing polymers, humectants, surfactants, preservatives, antioxidants, solvents, and fillers, antioxidants, solvents, perfumes, fillers, screening agents, bactericides, odor absorbers and coloring matter.

As oils which can be used in the invention, mineral oils (liquid paraffin), vegetable oils (liquid fraction of shea butter, sunflower oil), animal oils, synthetic oils, silicone oils (cyclomethicone) and fluorinated oils may be mentioned. Fatty alcohols, fatty acids (stearic acid) and waxes (paraffin, carnauba, beeswax) may also be used as fatty substances.

As emulsifiers which can be used in the invention, glycerol stearate, polysorbate 60 and the PEG-6/PEG-32/glycol stearate mixture are contemplated. As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned, and as lipophilic gelling agents, modified clays such as bentones, metal salts of fatty acids such as aluminum stearates and hydrophobic silica, or alternatively ethylcellulose and polyethylene may be mentioned.

As hydrophilic active agents, proteins or protein hydrolysates, amino acids, polyols, urea, allantoin, sugars and sugar derivatives, vitamins, starch and plant extracts, in particular those of Aloe vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features when utilized.

In addition, a surfactant can be included in the composition so as to provide deeper penetration of the compound capable of depleting mast cells, such as a tyrosine kinase inhibitor, preferably a c-kit and/or a bcr-abl inhibitor.

Among the contemplated ingredients, the invention embraces penetration enhancing agents selected for example from the group consisting of mineral oil, water, ethanol, triacetin, glycerin and propylene glycol; cohesion agents selected for example from the group consisting of polyisobutylene, polyvinyl acetate and polyvinyl alcohol, and thickening agents.

Chemical methods of enhancing topical absorption of drugs are well known in the art. For example, compounds with penetration enhancing properties include sodium lauryl sulfate (Dugard, P. H. and Sheuplein, R. J., "Effects of Ionic Surfactants on the Permeability of Human Epidermis: An Electrometric Study," J. Ivest. Dermatol., V.60, pp. 263-69, 1973), lauryl amine oxide (Johnson et al., U.S. Pat. No. 4,411, 893), azone (Rajadhyaksha, U.S. Pat. Nos. 4,405,616 and 3,989,816) and decylmethyl sulfoxide (Sekura, D. L. and Scala, J., "The Percutaneous Absorption of Alkylmethyl Sulfides," Pharmacology of the Skin, Advances In Biolocy of Skin, (Appleton-Century Craft) V. 12, pp. 257-69, 1972). It has been observed that increasing the polarity of the head group in amphoteric molecules increases their penetration-enhancing properties but at the expense of increasing their skin irritating properties (Cooper, E. R. and Berner, B., "Interaction of Surfactants with Epidermal Tissues: Physiochemical Aspects," Surfactant Science Series, V. 16, Reiger, M. M. ed. (Marcel Dekker, Inc.) pp. 195-210, 1987).

A second class of chemical enhancers are generally referred to as co-solvents. These materials are absorbed topically relatively easily, and, by a variety of mechanisms, achieve permeation enhancement for some drugs. Ethanol (Gale et. al., U.S. Pat. No. 4,615,699 and Campbell et. al., U.S. Pat. Nos. 4,460,372 and 4,379,454), dimethyl sulfoxide (U.S. Pat. Nos. 3,740,420 and 3,743,727, and U.S. Pat. No. 4,575,515), and glycerine derivatives (U.S. Pat. No. 4,322,433) are a few examples of compounds which have shown an ability to enhance the absorption of various compounds.

The pharmaceutical compositions of the invention can also be intended for administration with aerosolized formulation to target areas of a patient's respiratory tract.

Devices and methodologies for delivering aerosolized bursts of a formulation of a drug is disclosed in U.S. Pat. No. 5,906,202. Formulations are preferably solutions, e.g. aqueous solutions, ethanoic solutions, aqueous/ethanoic solutions, saline solutions, colloidal suspensions and microcrystalline suspensions. For example aerosolized particles comprise the active ingredient mentioned above and a carrier, (e.g., a pharmaceutically active respiratory drug and carrier) which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs.

The invention encompasses the systems described in U.S. Pat. No. 5,556,611:
  liquid gas systems (a liquefied gas is used as propellent gas (e.g. low-boiling FCHC or propane, butane) in a pressure container,
  suspension aerosol (the active substance particles are suspended in solid form in the liquid propellent phase),
  pressurized gas system (a compressed gas such as nitrogen, carbon dioxide, dinitrogen monoxide, air is used.

Thus, according to the invention the pharmaceutical preparation is made in that the active substance is dissolved or dispersed in a suitable nontoxic medium and said solution or dispersion atomized to an aerosol, i.e. distributed extremely finely in a carrier gas. This is technically possible for example in the form of aerosol propellent gas packs, pump aerosols or other devices known per se for liquid misting and solid atomizing which in particular permit an exact individual dosage.

Therefore, the invention is also directed to aerosol devices comprising the compound as defined above and such a formulation, preferably with metered dose valves.

The pharmaceutical compositions of the invention can also be intended for intranasal administration.

In this regard, pharmaceutically acceptable carriers for administering the compound to the nasal mucosal surfaces will be readily appreciated by the ordinary artisan. These carriers are described in the Remington's Pharmaceutical Sciences" 16th edition, 1980, Ed. By Arthur Osol, the disclosure of which is incorporated herein by reference.

The selection of appropriate carriers depends upon the particular type of administration that is contemplated. For administration via the upper respiratory tract, the composition can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's, Id. at page 1445). Of course, the ordinary artisan can readily determine a suitable saline content and pH for an innocuous aqueous carrier for nasal and/or upper respiratory administration.

Common intranasal carriers include nasal gels, creams, pastes or ointments with a viscosity of, e.g., from about 10 to about 3000 cps, or from about 2500 to 6500 cps, or greater, may also be used to provide a more sustained contact with the nasal mucosal surfaces. Such carrier viscous formulations may be based upon, simply by way of example, alkylcelluloses and/or other biocompatible carriers of high viscosity well known to the art (see e.g., Remington's, cited supra. A preferred alkylcellulose is, e.g., methylcellulose in a concentration ranging from about 5 to about 1000 or more mg per 100 ml of carrier. A more preferred concentration of methyl cellulose is, simply by way of example, from about 25 to about mg per 100 ml of carrier.

Other ingredients, such as art known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. For nasal administration of solutions or suspensions according to the invention, various devices are available in the art for the generation of drops, droplets and sprays.

A premeasured unit dosage dispenser including a dropper or spray device containing a solution or suspension for delivery as drops or as a spray is prepared containing one or more doses of the drug to be administered and is another object of the invention. The invention also includes a kit containing one or more unit dehydrated doses of the compound, together with any required salts and/or buffer agents, preservatives, colorants and the like, ready for preparation of a solution or suspension by the addition of a suitable amount of water.

Another aspect of the invention is directed to the use of said compound to manufacture a medicament. In other words, the invention embraces a method for treating a disease related to unregulated c-kit transduction comprising administering an effective amount of a compound as defined above to a mammal in need of such treatment. It also relates to a method for treating a disease related bcr-abl and/or Flt-3 comprising administering an effective amount of a compound as defined above to a mammal in need of such treatment.

More particularly, the invention is aimed at a method for treating a disease selected from autoimmune diseases, allergic diseases, bone loss, cancers such as leukemia and GIST, tumor angiogenesis, inflammatory diseases, inflammatory bowel diseases (IBD), interstitial cystitis, mastocytosis, infections diseases, metabolic disorders, fibrosis, diabetes and CNS disorders comprising administering an effective amount a compound depicted above to a mammal in need of such treatment.

The above described compounds are useful for manufacturing a medicament for the treatment of diseases related to unregulated c-kit transduction, including, but not limited to:
  neoplastic diseases such as mastocytosis, canine mastocytoma, solid tumours, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, solid tumors and astrocytomas.

tumor angiogenesis.

metabolic diseases such as diabetes mellitus and its chronic complications; obesity, type II diabetes; hyperlipidemias and dyslipidemias; atherosclerosis;

hypertension; and cardiovascular disease.

allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation.

interstitial cystitis.

bone loss (osteoporosis).

inflammatory diseases such as rheumatoid arthritis, conjunctivitis, rheumatoid spondylitis, osteoarthritis, gouty arthritis and other arthritic conditions as well as inflammatory muscle disorders;

autoimmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis.

graft-versus-host disease or graft rejection in any organ transplantation including kidney, pancreas, liver, heart, lung, and bone marrow.

Other autoimmune diseases embraced by the invention active chronic hepatitis and chronic fatigue syndrome.

subepidermal blistering disorders such as pemphigus.

Vasculitis.

HIV infection.

*Plasmodium* infection.

melanocyte dysfunction associated diseases such as hypermelanosis resulting from melanocyte dysfunction and including lentigines, solar and senile lentigo, Dubreuilh melanosis, moles as well as malignant melanomas. In this regard, the invention embraces the use of the compounds defined above to manufacture a medicament or a cosmetic composition for whitening human skin.

CNS disorders such as psychiatric disorders, migraine, pain, memory loss and nerve cells degeneracy. More particularly, the method according to the invention is useful for the treatment of the following disorders: Depression including dysthymic disorder, cyclothymic disorder, bipolar depression, severe or "melancholic" depression, atypical depression, refractory depression, seasonal depression, anorexia, bulimia, premenstrual syndrome, post-menopause syndrome, other syndromes such as mental slowing and loss of concentration, pessimistic worry, agitation, self-deprecation, decreased libido, pain including, acute pain, postoperative pain, chronic pain, nociceptive pain, cancer pain, neuropathic pain, psychogenic pain syndromes, anxiety disorders including anxiety associated with hyperventilation and cardiac arrhythmias, phobic disorders, obsessive-compulsive disorder, posttraumatic stress disorder, acute stress disorder, generalized anxiety disorder, psychiatric emergencies such as panic attacks, including psychosis, delusional disorders, conversion disorders, phobias, mania, delirium, dissociative episodes including dissociative amnesia, dissociative fugue and dissociative identity disorder, depersonalization, catatonia, seizures, severe psychiatric emergencies including suicidal behaviour, self-neglect, violent or aggressive behaviour, trauma, borderline personality, and acute psychosis, schizophrenia including paranoid schizophrenia, disorganized schizophrenia, catatonic schizophrenia, and undifferentiated schizophrenia, neurodegenerative diseases including Alzheimer's disease, Parkinson's disease, Huntington's disease, the prion diseases, Motor Neurone Disease (MND), and Amyotrophic Lateral Sclerosis (ALS).

substance use disorders as referred herein include but are not limited to drug addiction, drug abuse, drug habituation, drug dependence, withdrawal syndrome and overdose.

Cerebral ischemia

Fibrosis

Duchenne muscular dystrophy fibrodysplasia

ACNE as male contraceptive.

Regarding mastocytosis, the invention contemplates the use of the compounds as defined above for treating the different categories which can be classified as follows: The category I is composed by two sub-categories (IA and IB). Category IA is made by diseases in which mast cell infiltration is strictly localized to the skin. This category represents the most frequent form of the disease and includes: i) urticaria pigmentosa, the most common form of cutaneous mastocytosis, particularly encountered in children, ii) diffuse cutaneous mastocytosis, iii) solitary mastocytoma and iv) some rare subtypes like bullous, erythrodermic and teleangiectatic mastocytosis. These forms are characterized by their excellent prognosis with spontaneous remissions in children and a very indolent course in adults. Long term survival of this form of disease is generally comparable to that of the normal population and the translation into another form of mastocytosis is rare. Category IB is represented by indolent systemic disease (SM) with or without cutaneous involvement. These forms are much more usual in adults than in children. The course of the disease is often indolent, but sometimes signs of aggressive or malignant mastocytosis can occur, leading to progressive impaired organ fuction.

The category II includes mastocytosis with an associated hematological disorder, such as a myeloproliferative or myelodysplastic syndrome, or acute leukemia These malignant mastocytosis does not usually involve the skin. The progression of the disease depends generally on the type of associated hematological disorder that conditions the prognosis.

The category III is represented by aggressive systemic mastocytosis in which massive infiltration of multiple organs by abnormal mast cells is common. In patients who pursue this kind of aggressive clinical course, peripheral blood features suggestive of a myeloproliferative disorder are more prominent. The progression of the disease can be very rapid, similar to acute leukemia, or some patients can show a longer survival time.

Finally, the category IV of mastocytosis includes the mast cell leukemia, characterized by the presence of circulating mast cells and mast cell progenitors representing more than 10% of the white blood cells. This entity represents probably the rarest type of leukemia in humans, and has a very poor prognosis, similar to the rapidly progressing variant of malignant mastocytosis. Mast cell leukemia can occur either de novo or as the terminal phase of urticaria pigmentosa or systemic mastocytosis.

The invention also contemplates the method as depicted for the treatment of recurrent bacterial infections, resurging infections after asymptomatic periods such as bacterial cystitis. More particularly, the invention can be practiced for treating FimH expressing bacteria infections such as Gram-negative enterobacteria including *E. coli, Klebsiella pneumoniae, Serratia marcescens, Citrobactor freudii* and *Salmonella typhimurium*. In this method for treating bacterial infection, separate, sequential or concomitant administration of at least one antibiotic selected bacitracin, the cephalosporins, the penicillins, the aminoglycosides, the tetracyclines, the streptomycins and the macrolide antibiotics such as erythromycin; the fluoroquinolones, actinomycin, the sulfonamides and trimethoprim, is of interest.

In one preferred embodiment, the invention is directed to a method for treating neoplastic diseases such as mastocytosis, canine mastocytoma, solid tumours, human gastrointestinal stromal tumor ("GIST"), small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, and astrocytomas comprising administering a compound as defined herein to a human or mammal, especially dogs and cats, in need of such treatment.

In one other preferred embodiment, the invention is directed to a method for treating allergic diseases such as asthma, allergic rhinitis, allergic sinusitis, anaphylactic syndrome, urticaria, angioedema, atopic dermatitis, allergic contact dermatitis, erythema nodosum, erythema multiforme, cutaneous necrotizing venulitis and insect bite skin inflammation and blood sucking parasitic infestation comprising administering a compound as defined herein to a human or mammal, especially dogs and cats, in need of such treatment.

In still another preferred embodiment, the invention is directed to a method for treating inflammatory diseases such as rheumatoid arthritis, conjunctivitis, rheumatoid spondylitis, osteoarthritis, gouty arthritis and other arthritic conditions comprising administering a compound as defined herein to a human in need of such treatment.

In still another preferred embodiment, the invention is directed to a method for treating autoiunmune diseases such as multiple sclerosis, psoriasis, intestine inflammatory disease, ulcerative colitis, Crohn's disease, rheumatoid arthritis and polyarthritis, local and systemic scleroderma, systemic lupus erythematosus, discoid lupus erythematosus, cutaneous lupus, dermatomyositis, polymyositis, Sjogren's syndrome, nodular panarteritis, autoimmune enteropathy, as well as proliferative glomerulonephritis comprising administering a compound as defined herein to a human in need of such treatment.

In still another preferred embodiment, the invention is directed to a method for treating graft-versus-host disease or graft rejection in any organ transplantation including kidney, pancreas, liver, heart, lung, and bone marrow comprising administering a compound as defined herein to a human in need of such treatment.

EXAMPLE

In Vitro TK Inhibition Assays

Procedures

C-Kit WT and Mutated C-Kit (JM and Kinase Domain 816) Assay Proliferation Assays Cells were washed two times in PBS before plating at $5\times10^4$ cells per well of 96-well plates in triplicate and stimulated either with hematopoietic growth factors (HGF) or without After 2 days of culture, 37 Bq (1.78 Tbq/mmol) of [$_3$H] thymidine (Amersham Life Science, UK) was added for 6 hours. Cells were harvested and filtered through glass fiber filters and [$_3$H] thymidine incorporation was measured in a scintillation counter.

For proliferation assay, all drugs were prepared as 20 mM stock solutions in DMSO and conserved at −80° C. Fresh dilutions in PBS were made before each experiment. DMSO dissolved drugs were added at the beginning of the culture. Control cultures were done with corresponding DMSO dilutions. Results are represented in percentage by taking the proliferation without inhibitor as 100%.

Cells

Ba/F3 murine kit and human kit, Ba/F3 mkitΔ27 (juxtamembrane deletion), and hkitD816V are derived from the murine IL-3 dependent Ba/F3 proB lymphoid cells. The FMA3 and P815 cell lines are mastocytoma cells expressing endogenous mutated forms of Kit, i.e., frame deletion in the murine juxtamembrane coding region of the receptor-codons 573 to 579. The human leukaemic MC line HMC-1 expresses a double point mutation (i.e. mutations JM-V560G and the kinase domain mutation kitD816V), whereas the HMC1 subclone α155 expresses only the mutation JM-V560G.

Immunoprecipitation Assays and Western Blotting Analysis

For each assay, 5.106 Ba/F3 cells and Ba/F3-derived cells with various c-kit mutations were lysed and immunoprecipitated as described (Beslu et al., 1996), excepted that cells were stimulated with 250 ng/ml of rmKL. Cell lysates were immunoprecipitated with rabbit inmunsera directed against the KIT cytoplasmic domain either with an anti murine KIT (Rottapel et al., 1991) or an anti human KIT (Santa Cruz),. Western blot was hybridized either with the 4G10 anti-phosphotyrosine antibody (UBI) or with the appropriate rabbit immunsera anti KIT or with different antibodies (described in antibodies paragraph). The membrane was then incubated either with HRP-conjugated goat anti mouse IgG antibody or with HRP-conjugated goat anti rabbit IgG antibody (Immunotech), Proteins of interest were then visualized by incubation with ECL reagent (Amersham).

Experimental Results

The experimental results for various compounds according to the invention using above-described protocols are set forth at Table 1:

TABLE 1 in vitro inhibitions of various compounds against c-Kit WT, c-Kit JMΔ27 and c-Kit D816V.

| Target | IC50 (µM) | Compounds |
|---|---|---|
| c-Kit WT | IC50 < 1 µM | 005; 006; 008; 009; 019; 010; 011; 023; 025; 026; 027; 028; 029; 032; 033; 035; 036; 038; 039; 040; 041; 042; 043; 044; 048; 050; 055; 056; 057; 059; 061; 062: |
| c-Kit JM Δ27 | IC50 < 1 µM | 003; 004; 005; 006; 007; 008; 009; 010; 011; 012; 019; 022; 042; 050; 055; |
| c-Kit D816V | IC50 ≦ 1 µM | 023; 025; 026; 029; 032; 035; 036; 038; 039; 041; 042; 043; 044; 055; 059; 063; |

The invention claimed is:
1. A compound of formula I:

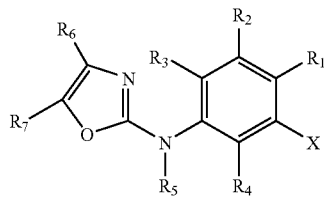

FORMULA I wherein substituents R1-R7 and X are defined as follows:
R1, R2, R3 and R4 each independently are selected from hydrogen, halogen (selected from F, Cl, Br or I), a linear or branched alkyl group containing from 1 to 10 carbon atoms and optionally substituted with one or more hetereoatoms such as halogen (selected from F, Cl, Br or I), oxygen, and nitrogen, the latter optionally in the form of a pendant basic nitrogen functionality; as well as trifluoromethyl, $C_{1-6}$alkyloxy, amino, $C_{1-6}$alkylamino, di($C_{1-6}$alkyl)amino, carboxyl, cyano, nitro, formyl, hydroxy, and CO—R, COO—R, CONH—R, and S02-R wherein R is a linear or branched alkyl group containing from 1 to 10 carbon atoms and optionally substituted with at least one heteroatom, notably a halogen (selected from F, CL, Br or I), oxygen, and nitrogen, the latter optionally in the form of a pendant basic nitrogen functionality;
R5 is one of the following:
(i) hydrogen, or
(ii) a linear or branched alkyl group containing from 1 to 10 carbon atoms and optionally substituted with one or more hetereoatoms such as halogen (selected from F, Cl, Br or I), oxygen, and nitrogen, the latter optionally in the form of a pendant basic nitrogen functionality, or
(iii) CO—R8 or COOR8 or CONHR8 or S02R8 wherein R8 may be
 a linear or branched alkyl group containing from 1 to 10 carbon atoms and optionally substituted with one or more hetereoatoms such as halogen (selected from F, Cl, Br or I), oxygen, and nitrogen, the latter optionally in the form of a pendant basic nitrogen functionality, or
 an aryl group such as phenyl or a substituted variant thereof bearing any combination, at any one ring position, of one or more substituents such as halogen (selected from F, Cl, Br or I), alkyl groups containing from 1 to 10 carbon atoms and optionally substituted with one or more hetereoatoms such as halogen (selected from F, Cl, Br or I), oxygen, and nitrogen, the latter optionally in the form of a pendant basic nitrogen functionality; as well as trifluoromethyl, $C_{1-6}$alkyloxy, carboxyl, cyano, nitro, formyl, hydroxy, $C_{1-6}$alkylamino, di($C_{1-6}$alkyl)amino, and amino, the latter nitrogen substituents optionally in the form of a pendant basic nitrogen functionality; as well as CO—R, COO—R, CONH—R, S02-R, and SO2NH—R wherein R is a linear or branched alkyl group containing from 1 to 10 carbon atoms and optionally substituted with at least one heteroatom, notably a halogen (selected from F, CL, Br or I), oxygen, and nitrogen, the latter optionally in the form of a pendant basic nitrogen functionality, or
 a heteroaryl group such as a pyridyl, pyrimidinyl, pyrazinyl, pyridazinyl, thienyl, thiazolyl, imidazolyl, pyrazolyl, pyrrolyl, furanyl, oxazolyl, isoxazolyl, triazolyl, tetrazolyl, indolyl, benzimidazole, quinolinyl group, which may additionally bear any combination, at any one ring position, of one or more substituents such as halogen (selected from F, Cl, Br or I), alkyl groups containing from 1 to 10 carbon atoms and optionally substituted with one or more hetereoatoms such as halogen (selected from F, Cl, Br or I), oxygen, and nitrogen, the latter optionally in the form of a pendant basic nitrogen functionality; as well as trifluoromethyl, $C_{1-6}$alkyloxy, carboxyl, cyano, nitro, formyl, hydroxy, $C_{1-6}$alkylamino, di($C_{1-6}$alkyl)amino, and amino, the latter nitrogen substituents optionally in the form of a pendant basic nitrogen functionality; as well as CO—R, COO—R, CONH—R, S02-R, and SO2NH—R wherein R is a linear or branched alkyl group containing from 1 to 10 carbon atoms and optionally substituted with at least one heteroatom, notably a halogen (selected from F, Cl, Br or I), oxygen, and nitrogen, the latter optionally in the form of a pendant basic nitrogen functionality,
R6 is selected from
i) hydrogen, a halogen (selected from F, Cl, Br or I), or
ii) an alkyl[1] group defined as a linear, branched or cycloalkyl group containing from 1 to 10 carbon atoms and optionally substituted with one or more hetereoatoms such as halogen (selected from F, Cl, Br or I), oxygen, and nitrogen (the latter optionally in the form of a pendant basic nitrogen functionality); as well as trifluoromethyl, carboxyl, cyano, nitro, formyl; as well as CO—R, COO—R, CONH—R, S02-R, and SO2NH—R wherein R is a linear or branched alkyl group containing 1 to 10 carbon atoms and optionally substituted with at least one heteroatom, notably a halogen (selected from F, Cl, Br or I), oxygen, and nitrogen, the latter optionally in the form of a pendant basic nitrogen functionality; as well as a cycloalkyl or aryl or heteroaryl group optionally substituted by a pendant basic nitrogen functionality, or
(iii) an aryl[1] group defined as phenyl or a substituted variant thereof bearing any combination, at any one ring position, of one or more substituents such as
 halogen (selected from I, F, Cl or Br);
 alkyl[1] group;
 a cycloakyl, aryl or heteroaryl group optionally substituted by a pendant basic nitrogen functionality;
 trifluoromethyl, O-alkyl[1] carboxyl, cyano, nitro, formyl, hydroxy, NH-alkyl[1], N(alkyl[1])(alkyl[1]), and amino, the latter nitrogen substituents optionally in the form of a basic nitrogen functionality;
 NHCO—R or NHCOO—R or NHCONH—R or NHS02-R or NHS02NH—R or CO—R or COO—R or CONH—R or S02-R or SO2NH—R wherein R corresponds to hydrogen, alkyl[1], aryl or heteroaryl, or
(iv) a heteroaryl[1] group defined as a pyridyl, pyrimidinyl, pyrazinyl, pyridazinyl, thienyl, thiazolyl, imidazolyl, pyrazolyl, pyrrolyl, furanyl, oxazolyl, isoxazolyl, triazolyl, tetrazolyl, indolyl, benzimidazole, quinolinyl group, which may additionally bear any combination, at any one ring position, of one or more substituents such as
 halogen (selected from F, Cl, Br or I);
 an alkyl[1] group;
 a cycloakyl, aryl or heteroaryl group optionally substituted by a pendant basic nitrogen functionality, trifluoromethyl, O-alkyl¹ carboxyl, cyano, nitro, formyl, hydroxy, NH-(alkyl¹), alkyl¹, N(alkyl¹)(alkyl¹), and amino, the latter nitrogen substituents optionally in the form of a basic nitrogen functionality;

NHCO—R or NHCOO—R or NHCONH—R or NHS02-R or NHS02NH—R or CO—R or COO—R or CONH—R or S02-R or SO2NH—R wherein R corresponds to hydrogen, alkyl¹, or (v) an O-aryl¹, or NH-aryl¹, or O-heteroaryl¹ group (vi) trifluoromethyl, O-alkyl¹, carboxyl, cyano, nitro, formyl, hydroxy, NH-alkyl¹, N(alkyl¹)(alkyl¹), and amino, the latter nitrogen substituents optionally in the form of a basic nitrogen functionality, or (vii) NHCO—R or NHCOO—R or NHCONH—R or NHS02-R or NHS02NH—R or CO—R or COO—R or CONH—R or S02-R or SO2NH—R wherein R corresponds to hydrogen, alkyl¹, aryl or heteroaryl, R7 is selected from:

(iv) a heteroaryl¹ group defined as a pyridyl, pyrimidinyl, pyrazinyl, pyridazinyl, thienyl, thiazolyl, imidazolyl, pyrazolyl, pyrrolyl, furanyl, oxazolyl, isoxazolyl, triazolyl, tetrazolyl, indolyl, benzimidazole, quinolinyl group, which may additionally bear any combination, at any one ring position, of one or more substituents such as halogen (selected from F, Cl, Br or I);

an alkyl¹ group;

a cycloakyl, aryl or heteroaryl group optionally substituted by a pendant basic nitrogen functionality, trifluoromethyl, O-alkyl¹ carboxyl, cyano, nitro, formyl, hydroxy, NH-(alkyl¹), alkyl¹, N(alkyl¹)(alkyl¹), and amino, the latter nitrogen substituents optionally in the form of a basic nitrogen functionality;

NHCO—R or NHCOO—R or NHCONH—R or NHS02-R or NHS02NH—R or CO—R or COO—R or CONH—R or S02-R or SO2NH—R wherein R corresponds to hydrogen, alkyl¹, or X is:

—NR9R10, wherein R9 and/or R10 are hydrogen or:

i) an alkyl¹ group, CF3 or ii) an aryl¹, heteroaryl¹ or cycloalkyl group optionally substituted by a pendant basic nitrogen functionality, or iii) a CO—R, COO—R, CON—RR' or S02-R, where R and R' are a hydrogen, alkyl¹, aryl¹, or heteroaryl¹, optionally substituted by a pendant basic nitrogen functionality; or:

—CO—NR9R10, wherein R9 and/or R10 are hydrogen or:

i) an alkyl¹ group, CF3 or ii) an aryl¹, heteroaryl¹, or cycloalkyl group optionally substituted by a pendant basic nitrogen functionality.

2. A compound according to claim 1 wherein X is NR9R10, R9 is H, and R10 is alkyl¹.

3. A compound according to claim 1 of formula II:

FORMULA II

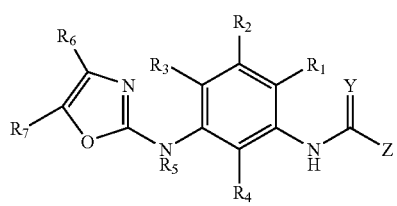

Wherein Y is selected from O, and Z corresponds to H, NRaRb, alkyl¹, aryl¹, O-alkyl¹, or O-aryl¹, or wherein Ra and Rb are independently chosen from H or alkyl¹ or aryl¹ or heteroaryl¹, optionally substituted by a pendant basic nitrogen functionality.

4. A compound according to claim 1 of formula II-1:

FORMULA II-1

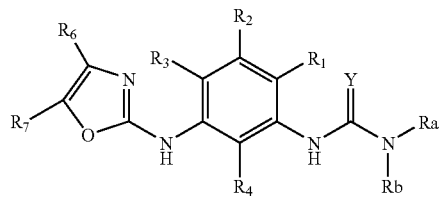

Wherein R5=H, Y=O S and Ra, Rb are independently chosen from H or alkyl¹ or aryl¹ or heteroaryl¹, optionally substituted by a pendant basic nitrogen functionality.

5. A compound of formula II-2:

FORMULA II-2

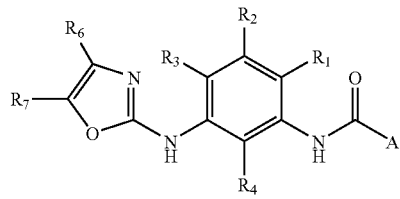

Wherein A is aryl¹ or heteroaryl¹ and wherein R1, R2, R3, R4, R6, R7, aryl¹, heteroaryl¹ have the meaning as defined in claim 1.

6. A compound of formula II-3:

FORMULA II-3

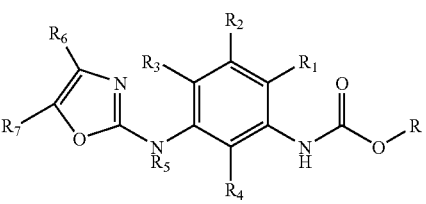

Wherein R is independently alkyl¹, aryl¹, or heteroary¹ and wherein R1, R2, R3, R4, R5, R6, and R7 have the meaning described as defined in claim 1.

7. A compound according to claim 1 of formula II-4:

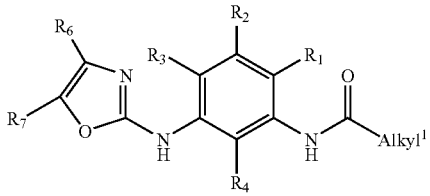

FORMULA II-4

8. A compound of formula I-3:

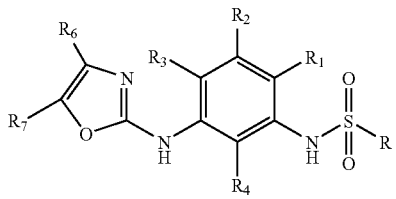

FORMULA I-3

Wherein X is NHS02R group, R is independently alkyl¹, aryl¹, or heteroaryl¹ and wherein, alkyl¹, aryl¹, or heteroary¹, R1, R2, R3, R4, R6 and R7 have the meaning as defined in claim 1.

9. A compound according to claim 1 of formula III:

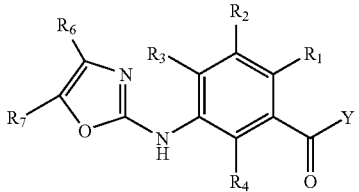

FORMULA III

Wherein Y is selected from NRaRb, alkyl¹, aryl¹, Ra wherein Ra and Rb are independently chosen from H or alkyl¹ or aryl¹ or heteroaryl, optionally substituted by a pendant basic nitrogen functionality.

10. A compound as claimed in claim 1 selected from:
4-{[4-Methyl-3-(4-pyridin-3-yl-oxazol-2-ylamino)-phenylamino]-methyl}-benzoic acid methyl ester;
4-Methyl-N1-(5-pyridin-3-yl-oxazol-2-yl)-N3-(5-pyridin-4-yl-oxazol-2-yl)-benzene-1,3-diamine;
4-Methyl-N1-(5-phenyl-oxazol-2-yl)-N3-(5-pyridin-4-yl-oxazol-2-yl)-benzene-1,3-diamine;
4-Methyl-N1-(5-phenyl-[1,3,4]oxadiazol-2-yl)-N3-(5-pyridin-4-yl-oxazol-2-yl)-benzene-1,3-diamine;
N1-Benzooxazol-2-yl-4-methyl-N3-(5-pyridin-4-yl-oxazol-2-yl)-benzene-1,3-diamine;
N-[4-Methyl-3-(5-pyridin-3-yl-oxazol-2-ylamino)-phenyl]-acetamide;
2-Cyano-N-[4-methyl-3-(5-pyridin-4-yl-oxazol-2-ylamino)-phenyl]-acetamide;
2-Ethoxy-N-[4-methyl-3-(5-pyridin-3-yl-oxazol-2-ylamino)-phenyl]-acetamide;
3-Methoxy-N-[4-methyl-3-(5-pyridin-3-yl-oxazol-2-ylamino)-phenyl]-propionamide;
1-[4-Methyl-3-(5-pyridin-3-yl-oxazol-2-ylamino)-phenyl]-3-p-tolyl-urea;
1-(4-Cyano-phenyl)-3-[4-methyl-3-(5-pyridin-3-yl-oxazol-2-ylamino)-phenyl]-urea;
1-(4-Fluoro-phenyl)-3-[4-methyl-3-(5-pyridin-3-yl-oxazol-2-ylamino)-phenyl]-urea;
1-(2-Fluoro-phenyl)-3-[4-methyl-3-(5-pyridin-3-yl-oxazol-2-ylamino)-phenyl]-urea;
1-[4-Methyl-3-(5-pyridin-3-yl-oxazol-2-ylamino)-phenyl]-3-(4-trifluoromethyl-phenyl)-urea;
1-(4-Chloro-phenyl)-3-[4-methyl-3-(5-pyridin-3-yl-oxazol-2-ylamino)-phenyl]-urea;
1-[4-Methyl-3-(5-phenyl-oxazol-2-ylamino)-phenyl]-3-(3-trifluoromethyl-phenyl)-urea;
1-(4-Cyano-phenyl)-3-[4-methyl-3-(5-pyridin-3-yl-oxazol-2-ylamino)-phenyl]-thiourea;
1-(4-Cyano-phenyl)-3-[4-methyl-3-(5-pyridin-4-yl-oxazol-2-ylamino)-phenyl]-thiourea;
(2-{2-Methyl-5-[3-(4-trifluoromethyl-phenyl)-ureido]-phenylamino}-oxazol-5-yl)-acetic acid ethyl ester;
1-Benzyl-3-[4-methyl-3-(5-pyridin-4-yl-oxazol-2-ylamino)-phenyl]-thiourea;
4-(4-Methyl-piperazin-1-ylmethyl)-N-[4-methyl-3-(5-pyridin-3-yl-oxazol-2-ylamino)-phenyl]-benzamide;
3-Dimethylamino-N-[4-methyl-3-din-3-yl-oxazol-2-ylamino)-phenyl]-benzamide;
3-Bromo-N-[4-methyl-3-(5-pyridin-3-yl-oxazol-2-ylamino)-phenyl]-benzamide;
N-[4-Methoxy-3-(5-pyridin-3-yl-oxazol-2-ylamino)-phenyl]-3-trifluoromethyl-benzamide;
4-(3-Dimethylamino-propylamino)-N [4-methyl-3-(5-pyridin-3-yl-oxazol-2-ylamino)-phenyl]-3-trifluoromethyl-benzamide;
N-[4-Fluoro-3-(5-pyridin-3-yl-oxazol-2-ylamino)-phenyl]-3-trifluoromethyl-benzamide;
1H-hidole-6-carboxylic acid [4-methyl-3-(5-pyridin-4-yl-oxazol-2-ylamino)-phenyl]-amide;
3-Isopropoxy-N-[4-methyl-3-(5-pyridin-4-yl-oxazol-2-ylamino)-phenyl]-benzamide;
N-[4-Methyl-3-(5-pyridin-2-yl-oxazol-2-ylamino)-phenyl]-3-trifluoromethyl-benzamide;
3,5-Dimethoxy-N [4-methyl-3-(5-pyridin-4-yl-oxazol-2-ylamino)-phenyl]-benzamide;
N-[3-(5-Pyridin-3-yl-oxazol-2-ylamino)-phenyl]-3-trifluoromethyl-benzamide;
N-[4-Methyl-3-(5-phenyl-oxazol-2-ylamino)-phenyl]-3-trifluoromethyl-benzamide;
3-Fluoro-4-(4-methyl-piperazin-1-ylmethyl)-N-[4-methyl-3-(5-pyridin-3-yl-oxazol-2-ylamino)-phenyl]-benzamide;
N-[4-Chloro-3-(5-pyridin-3-yl-oxazol-2-ylamino)-phenyl]-3-trifluoromethyl-benzamide;
N-[4-Methyl-3-(5-pyridin-3-yl-oxazol-2-ylamino)-phenyl]-terephthalamide;
5-Methyl-isoxazole-4-carboxylic acid [4-methyl-3-(5-pyridin-4-yl-oxazol-2-ylamino)-phenyl]-amide;
4-Cyano-N-[4-methyl-3-(5-pyridin-4-yl-oxazol-2-ylamino)-phenyl]-benzamide;
N-[4-Methyl-3-(5-pyridin-3-yl-oxazol-2-ylamino)-phenyl]-isonicotinamide;
N-[4-Methyl-3-(4-pyridin-3-yl-oxazol-2-ylamino)-phenyl]-3-trifluoromethyl-benzamide;
[4-Methyl-3-(5-pyridin-3-yl-oxazol-2-ylamino)-phenyl]-carbamic acid isobutyl ester;
(5-Isobutoxycarbonylamino-2-methyl-phenyl)-(5-pyridin-3-yl-oxazol-2-yl)-carbamic acid isobutyl ester;

[4-Methyl-3-(5-pyridin-4-yl-oxazol-2-ylamino)-phenyl]-carbamic acid isobutyl ester;
N-[4-Methyl-3-(5-pyridin-4-yl-oxazol-2-ylamino)-phenyl]-2-m-tolyl-acetamide;
2-(4-Fluoro-phenyl)-N-[4-methoxy-3-(5-pyridin-4-yl-oxazol-2-yloamino)-phenyl]-acetamide;
2-(2,4-Difluoro-phenyl)-N-[4-methyl-3-(5-phenyl-oxazol-2-ylamino)-phenyl]-acetamide;
2-(3-Bromo-phenyl)-N-[4-methyl-3-(5-pyridin-2-yl-oxazol-2-ylamino)-phenyl]-acetamide;
3-(4-Fluoro-phenyl)-N-[4-methyl-3-(5-pyridin-4-yl-oxazol-2-ylamino)-phenyl]-propionamide;
2-(4-Fluoro-phenyl)-N [4-methyl-3-(5-pyridin-3-yl-oxazol-2-ylamino)-phenyl]-acetamide;
N-{3-[5-(4-Cyano-phenyl)-oxazol-2-ylamino]-4-methyl-phenyl}-2-(2,4-difluoro-phenyl)-acetamide;
4-Methyl-pentanoic acid [4-methyl-3-(5-pyridin-3-yl-oxazol-2-ylamino)-phenyl]-amide;
N-[4-Methyl-3-(5-pyridin-3-yl-oxazol-2-ylamino)-phenyl]-2-piperazin-1-yl-acetamide;
N [4-Methyl-3-(5-pyridin-3-yl-oxazol-2-ylamino)-phenyl]-3-piperazin-1-yl-propionamide;
2-(2,6-Dichloro-phenyl)-N [4-methyl-3-(5-pyridin-4-yl-oxazol-2-ylamino)-phenyl]-acetamide;
N-[4-Methyl-3-(5-pyridin-3-yl-oxazol-2-ylamino)-phenyl]-3-pyrrolidin-1-yl-propionamide;
N-[4-Methoxy-3-(5-pyridin-4-yl-oxazol-2-ylamino)-phenyl]-2-(4-trifluoromethyl-phenyl)-acetamide;
2-(4-Methoxy-phenyl)-N-[4-methyl-3-(5-pyridin-4-yl-oxazol-2-ylamino)-phenyl]-acetamide;
N-[4-Methyl-3-(5-pyridin-4-yl-oxazol-2-ylamino)-phenyl]-C-phenyl-methanesulfon-amide;
N-(4-Cyano-phenyl)-4-methyl-3-(5-pyridin-3-yl-oxazol-2-ylamino)-benzamide;
N-(3-Dimethylamino-phenyl)-4-methyl-3-(5-pyridin-4-yl-oxazol-2-ylamino)-benzamide;
N-(2-Dimethylamino-ethyl)-4-methyl-3-(5-pyridin-3-yl-oxazol-2-ylamino)-benzamide;
N-(3-Fluoro-4-methyl-phenyl)-4-methyl-3-(5-pyridin-4-yl-oxazol-2-ylamino)-benzamide;
N-(3-Chloro-phenyl)-4-methyl-3-(5-pyridin-3-yl-oxazol-2-ylamino)-benzamide;
N-Benzyl-4-methyl-3-(5-pyridin-4-yl-oxazol-2-ylamino)-benzamide;
N-(4-Methoxy-benzyl)-4-methyl-3-(5-pyridin-4-yl-oxazol-2-ylamino)-benzamide;
[4-Methyl-3-(5-pyridin-4-yl-oxazol-2-ylamino)-phenyl]-morpholin-4-yl-methanone;
[4-Methyl-3-(5-pyridin-4-yl-oxazol-2-yla. inino)-phenyl]-piperazin-1-yl-methanone;
N-(4-Fluoro-phenyl)-2-[4-methyl-3-(5-pyridin-4-yl-oxazol-2-ylamino)-phenyl]-acetamide.

11. A compound according to claim 1, wherein R6 is hydrogen and R7 is pyridyl, which may additionally bear any combination, at any one ring position, of one or more substituents such as halogen (selected from F, Cl, Br or I);
an alkyl$^1$ group;
an aryl$^1$ group;
trifluoromethyl, O-alkyl$^1$, carboxyl, cyano, nitro, formyl, hydroxy, NH-alkyl$^1$, N(alkyl$^1$)(alkyl$^1$), and amino, the latter nitrogen substituents optionally in the of a basic nitrogen functionality; or
NHCOO—R or NHCONH—R or NHSO2—R or NHSO2NH—R or CO—R or COO—R or CONH—R or SO2-R or SO2NH—R wherein R corresponds to hydrogen, alkyl or group.

12. A pharmaceutical composition comprising a compound according to claim 1.

13. A pharmaceutical composition according to claim 12 further comprising a pharmaceutically acceptable carrier.

14. A pharmaceutical composition according to claim 13 formulated as tablets, pills, dragees, capsules, liquids, gels, syrups, and suspensions.

15. A cosmetic or pharmaceutical composition for topical administration comprising a compound according to claim 1.

16. A method for treatment of an inflammatory disease which comprises administering to a patient in need thereof, an effective amount of a compound of claim 1,
wherein the inflammatory disease is selected from the group consisting of rheumatoid arthritis, conjunctivitis, rheumatoid spondylitis, osteoarthritis, gouty arthritis and other arthritic conditions.

17. A method for treatment of graft-versus-host disease or graft rejection in any organ transplantation including kidney, pancreas, liver, heart, lung, and bone marrow which comprises administering to a patient in need thereof, an effective amount of a compound of claim 1.

* * * * *

UNITED STATES PATENT AND TRADEMARK OFFICE
CERTIFICATE OF CORRECTION

| | | |
|---|---|---|
| PATENT NO. | : 7,718,676 B2 | Page 1 of 1 |
| APPLICATION NO. | : 10/576267 | |
| DATED | : May 18, 2010 | |
| INVENTOR(S) | : Moussy | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 765 days.

Signed and Sealed this
Fifteenth Day of February, 2011

David J. Kappos
*Director of the United States Patent and Trademark Office*